United States Patent
Manning et al.

(10) Patent No.: US 9,662,396 B2
(45) Date of Patent: *May 30, 2017

(54) STABLE AQUEOUS FORMULATIONS OF ETANERCEPT

(71) Applicant: Coherus Biosciences, Inc., Redwood City, CA (US)

(72) Inventors: Mark Manning, Johnstown, CO (US); Brian Murphy, Fort Collins, CO (US)

(73) Assignee: Coherus Biosciences, Inc., Redwood City, CA (US)

( * ) Notice: Subject to any disclaimer, the term of this patent is extended or adjusted under 35 U.S.C. 154(b) by 103 days.

This patent is subject to a terminal disclaimer.

(21) Appl. No.: 14/592,654

(22) Filed: Jan. 8, 2015

(65) Prior Publication Data

US 2015/0196645 A1 Jul. 16, 2015

Related U.S. Application Data

(63) Continuation of application No. PCT/US2013/049716, filed on Jul. 9, 2013.

(60) Provisional application No. 61/669,480, filed on Jul. 9, 2012, provisional application No. 61/806,235, filed on Mar. 28, 2013.

(51) Int. Cl.

| | | |
|---|---|---|
| *C07K 14/715* | (2006.01) |
| *A61K 38/17* | (2006.01) |
| *A61K 47/02* | (2006.01) |
| *C07K 19/00* | (2006.01) |
| *A61K 47/26* | (2006.01) |
| *A61K 9/14* | (2006.01) |
| *A61K 47/18* | (2017.01) |
| *A61K 47/22* | (2006.01) |
| *A61K 47/34* | (2017.01) |
| *C07K 16/24* | (2006.01) |
| *A61K 47/10* | (2017.01) |
| *C07K 14/705* | (2006.01) |
| *A61K 39/00* | (2006.01) |

(52) U.S. Cl.
CPC ............... *A61K 47/26* (2013.01); *A61K 9/14* (2013.01); *A61K 38/1793* (2013.01); *A61K 47/02* (2013.01); *A61K 47/10* (2013.01); *A61K 47/183* (2013.01); *A61K 47/22* (2013.01); *A61K 47/34* (2013.01); *C07K 14/70578* (2013.01); *C07K 14/7151* (2013.01); *C07K 16/241* (2013.01); *C07K 19/00* (2013.01); *A61K 2039/505* (2013.01); *C07K 2317/76* (2013.01); *C07K 2319/00* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,580,856 A | 12/1996 | Prestrelski et al. |
| 6,171,586 B1 | 1/2001 | Lam et al. |
| 7,648,702 B2 | 1/2010 | Gombotz et al. |
| 2007/0243185 A1* | 10/2007 | Gombotz et al. ......... 424/130.1 |
| 2012/0048587 A1 | 3/2012 | Gombotz et al. |
| 2013/0209465 A1 | 8/2013 | Jezek et al. |
| 2014/0255400 A1* | 9/2014 | Maloney et al. ......... 424/134.1 |

FOREIGN PATENT DOCUMENTS

| | | |
|---|---|---|
| EP | 1607103 A1 | 12/2005 |
| EP | 1478394 B1 | 7/2008 |
| EP | 2 699 265 A1 | 2/2014 |
| EP | 2 714 009 A1 | 4/2014 |
| EP | 2 726 090 A1 | 5/2014 |
| EP | 2 768 854 A1 | 8/2014 |
| WO | 00/62790 A2 | 10/2000 |
| WO | 03/072060 A2 | 9/2003 |
| WO | 2008/045373 A2 | 4/2008 |
| WO | 2011/141926 A2 | 11/2011 |
| WO | 2012/013980 A1 | 2/2012 |

OTHER PUBLICATIONS

Magnesium Chloride Solution Sigma Product Information (MCSSPI) sheet, published Dec. 2002, 1 page as printed.*
Caporali et al. "Diffuse skin reaction after changing the etanercept formulation", Clinical and Experimental Rheumatology, vol. 26, No. 6, (Nov. 1, 2008), p. 1165 XP055163902.
Gokarn, Y. R. et al. "Excipients for protein drugs" Excipient Development for Pharmaceutical, Biotechnology, and Drug Delivery Systems, Jan. 2006, p. 291-331; XP 009179656.
Zimmer, A. "Galenische Formulierung rekombinanter Wirkstoffe: Problem Arzneistoffstabilitat", Pharmazie in Unserer Zeit, Sep. 2003, 32(5)384-389; XP055109543.
Supplemental European Search Report for corresponding patent application EP 13 817 186.3 mailed Mar. 9, 2016.

* cited by examiner

*Primary Examiner* — Zachary Howard
(74) *Attorney, Agent, or Firm* — Wood, Phillips, Katz, Clark & Mortimer

(57) ABSTRACT

The invention provides stabilized aqueous pharmaceutical etanercept compositions suitable for long-term storage of etanercept, methods of manufacture of these compositions, methods of administration, and kits containing same.

4 Claims, No Drawings

SEQUENCE LISTING

```
<160> NUMBER OF SEQ ID NOS: 1

<210> SEQ ID NO 1
<211> LENGTH: 467
<212> TYPE: PRT
<213> ORGANISM: artificial sequence
<220> FEATURE:
<223> OTHER INFORMATION: Fusion protein between extracellular ligand
      binding portion of human 75 kilodalton tumor necrosis receptor
      and constant (Fc) portion of human IgG1 antibody.

<400> SEQUENCE: 1

Leu Pro Ala Gln Val Ala Phe Thr Pro Tyr Ala Pro Glu Pro Gly Ser
1               5                   10                  15

Thr Cys Arg Leu Arg Glu Tyr Tyr Asp Gln Thr Ala Gln Met Cys Cys
            20                  25                  30

Ser Lys Cys Ser Pro Gly Gln His Ala Lys Val Phe Cys Thr Lys Thr
        35                  40                  45

Ser Asp Thr Val Cys Asp Ser Cys Glu Asp Ser Thr Tyr Thr Gln Leu
    50                  55                  60

Trp Asn Trp Val Pro Glu Cys Leu Ser Cys Gly Ser Arg Cys Ser Ser
65                  70                  75                  80

Asp Gln Val Glu Thr Gln Ala Cys Thr Arg Glu Gln Asn Arg Ile Cys
                85                  90                  95

Thr Cys Arg Pro Gly Trp Tyr Cys Ala Leu Ser Lys Gln Glu Gly Cys
            100                 105                 110

Arg Leu Cys Ala Pro Leu Arg Lys Cys Arg Pro Gly Phe Gly Val Ala
        115                 120                 125

Arg Pro Gly Thr Glu Thr Ser Asp Val Val Cys Lys Pro Cys Ala Pro
    130                 135                 140

Gly Thr Phe Ser Asn Thr Thr Ser Ser Thr Asp Ile Cys Arg Pro His
145                 150                 155                 160
```

```
Gln Ile Cys Asn Val Val Ala Ile Pro Gly Asn Ala Ser Met Asp Ala
            165                 170                 175

Val Cys Thr Ser Thr Ser Pro Thr Arg Ser Met Ala Pro Gly Ala Val
            180                 185                 190

His Leu Pro Gln Pro Val Ser Thr Arg Ser Gln His Thr Gln Pro Thr
            195                 200                 205

Pro Glu Pro Ser Thr Ala Pro Ser Thr Ser Phe Leu Leu Pro Met Gly
        210                 215                 220

Pro Ser Pro Pro Ala Glu Gly Ser Thr Gly Asp Glu Pro Lys Ser Cys
225                 230                 235                 240

Asp Lys Thr His Thr Cys Pro Pro Cys Pro Ala Pro Glu Leu Leu Gly
            245                 250                 255

Gly Pro Ser Val Phe Leu Phe Pro Pro Lys Pro Lys Asp Thr Leu Met
            260                 265                 270

Ile Ser Arg Thr Pro Glu Val Thr Cys Val Val Val Asp Val Ser His
            275                 280                 285

Glu Asp Pro Glu Val Lys Phe Asn Trp Tyr Val Asp Gly Val Glu Val
        290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
            325                 330                 335

Lys Glu Tyr Lys Cys Lys Val Ser Asn Lys Ala Leu Pro Ala Pro Ile
            340                 345                 350

Glu Lys Thr Ile Ser Lys Ala Lys Gly Gln Pro Arg Glu Pro Gln Val
            355                 360                 365

Tyr Thr Leu Pro Pro Ser Arg Glu Glu Met Thr Lys Asn Gln Val Ser
        370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
            405                 410                 415

Val Leu Asp Ser Asp Gly Ser Phe Phe Leu Tyr Ser Lys Leu Thr Val
            420                 425                 430

Asp Lys Ser Arg Trp Gln Gln Gly Asn Val Phe Ser Cys Ser Val Met
            435                 440                 445

His Glu Ala Leu His Asn His Tyr Thr Gln Lys Ser Leu Ser Leu Ser
        450                 455                 460

Pro Gly Lys
465
```

STABLE AQUEOUS FORMULATIONS OF ETANERCEPT

FIELD OF THE INVENTION

The present invention relates to aqueous pharmaceutical compositions stabilized for long-term storage of etanercept, methods of manufacture of the compositions, methods of their administration, and kits containing the same. The invention includes etanercept formulations that do not require arginine for stabilization.

BACKGROUND OF THE INVENTION

Polypeptides must often be stored prior to their use. When stored for extended periods, polypeptides are frequently unstable in solution (Manning et al., 1989, Pharm. Res. 6:903-918). To extend their shelf life, additional processing steps have been developed, such as drying, e.g., lyophilization. However, lyophilized pharmaceutical compositions are less convenient to use.

Typical practices to improve polypeptide stability can be addressed by varying the concentration of elements with the formulation, or by adding excipients to modify the formulation (See, for example, U.S. Pat. Nos. 5,580,856 and 6,171,586). However, the use of additives can still result in inactive polypeptides. In addition, in the case of lyophilization, the rehydration step can result in inactivation of the polypeptide by, for example, aggregation or denaturation (Flora et al., 1992, Pharm. Res., 9:33-36; Liu et al., 1991, Biotechnol. Bioeng., 37:177-184). Aggregation of polypeptides is undesirable, as it may result in immunogenicity (Cleland et al., 1993, Crit. Rev. Therapeutic Drug Carrier Systems, 10:307-377; and Robbins et al., 1987, Diabetes, 36:838-845).

Another way to improve polypeptide stability is to use L-arginine at a specific concentration (U.S. Pat. No. 7,648,702).

One of the polypeptides that is often stored prior to use is etanercept (Enbrel®, Immunex Corporation), which is a dimeric fusion polypeptide consisting of the extracellular ligand-binding portion of the human 75 kilodalton (p75) tumor necrosis factor receptor (TNFR) linked to the Fc portion of human IgG1. It consists of 934 amino acids and has an apparent molecular weight of approximately 150 kilodaltons (Physicians Desk Reference, 2002, Medical Economics Company Inc.) The Fc component of etanercept contains the constant heavy 2 (CH2) domain, the constant heavy 3 (CH3) domain and hinge region, but not the constant heavy 1 (CH1) domain of human IgG1. An Fc domain can contain one or all of the domains described above. Etanercept is usually produced by recombinant DNA technology in a Chinese hamster ovary (CHO) mammalian cell expression system.

The present invention provides novel stable liquid formulations of etanercept that allow its long term storage.

SUMMARY OF THE INVENTION

In one embodiment, the invention provides a stable aqueous pharmaceutical composition comprising etanercept and a stabilizer to inhibit instability, aggregation and/or fragmentation of the etanercept, wherein the stabilizer comprises a compound selected from the group consisting of serine, proline and glutamate. In a preferred embodiment, the stabilizer comprises glutamate.

In another embodiment, the invention provides a stabilized aqueous pharmaceutical composition comprising etanercept and a stabilizer to inhibit instability, aggregation and/or fragmentation of the etanercept, wherein said stabilizer comprises a stabilizing metal ion. In a preferred embodiment, the metal ion is selected from the group consisting of calcium, magnesium, zinc, and combinations thereof. In an even more preferred embodiment, calcium, magnesium, zinc are provided as calcium chloride, magnesium chloride and zinc chloride, respectively. Calcium chloride and magnesium chloride are particularly preferred as stabilizers for etanercept.

In another embodiment, the invention provides a stabilized aqueous pharmaceutical composition comprising etanercept and a stabilizer to inhibit instability, aggregation and/or fragmentation of the etanercept, wherein said stabilizer is selected from the group consisting of ionic polyol derivatives, such as meglumine, mannosylglycerate, glucosylglycerate, mannosyllactate, mannosylglycolate, and diglycerolphosphate. In this embodiment, a preferred aqueous stabilized formulation of etanercept comprises: etanercept; and stabilizing ingredients to retard instability, aggregation and fragmentation of the etanercept in the formulation, said stabilizing ingredients being comprised of (a) meglumine; or (b) meglumine in combination with sucrose; or (c) meglumine in combination with sodium chloride; or (d) meglumine in combination with sodium chloride and sucrose.

In yet another embodiment, the invention provides a stable aqueous formulation comprising about 25 to about 75 mg/ml of etanercept, and a stabilizer to inhibit instability, aggregation and/or fragmentation of the etanercept, wherein said stabilizer comprises the combination of a sugar and a polyol. Preferably, the sugar is sucrose and the polyol is selected from the group consisting of mannitol and sorbitol. In a further aspect of this embodiment, the sugar is dextrose and the polyol is selected from the group consisting of mannitol and sorbitol. In a particularly preferred example of this embodiment, the invention is directed to stabilized etanercept formulation wherein a combination of sucrose and mannitol is present to provide stabilization of the etanercept monomer.

In a further embodiment, the invention provides an aqueous etanercept formulation stabilized to reduce instability, aggregation and/or fragmentation of the etanercept, said formulation comprising about 25 to about 75 mg/ml of etanercept and one or more stabilizers, wherein the stabilizers are selected from the group consisting of (i) sodium chloride and (ii) sodium chloride in combination with sucrose or trehalose; and (iii) a combination of sodium chloride, sucrose and trehalose.

In still another embodiment, the invention provides a stabilized aqueous pharmaceutical composition comprising etanercept and a stabilizer to inhibit instability, aggregation and/or fragmentation of the etanercept, wherein the stabilizer comprises xylitol or a combination of xylitol and meglumine.

Unlike commercially available etanercept, we found it surprising that each of the formulation embodiments of etanercept described and exemplified herein do not require arginine for long term stabilization, although arginine may still be added if desired. The ability to provide etanercept formulations stabilized without arginine represents a potentially significant benefit to the health care system by providing patients and health care providers with alternative formulations of etanercept that may become available at lower cost compared with present commercial etanercept formulation (i.e., Enbrel®) that require arginine for stabilization.

As used herein the term "instability" or like terms denotes the tendency of the etanercept monomer to undergo a variety of undesired transformations during storage. Such transformations include the formation of very high molecular weight aggregate(s) in which multiple copies of the essentially intact etanercept monomer become randomly associated with one another through a variety of non-covalent attractions (e.g., electrostatic interactions.) Undesired transformations during storage may also include degradation of the etanercept monomer to smaller fragments and/or oligomers. Ideally, a formulaton of etanercept should minimize, to the greatest extent possible, the tendency of the formulation to result, during storage, in the formation of aggregates, oligomers and/or fragments of the etanercept monomer. An important benefit resulting from the ability to reduce formation of unwanted aggregates or fragments is a reduction in the immunogenicity of the drug.

Each of the embodiments referenced above may be provided in a formulation which is optionally free, or essentially free of arginine. The term "essentially free of arginine" is intended to mean that arginine, even if present, is not contributing to the stabilization of the etanercept monomer in the formulation to such an extent that a person skilled in the art would judge its presence beneficial from a stabilization standpoint.

These and other aspects will become apparent from the following description of the various embodiments, although variations and modifications therein may be affected without departing from the spirit and scope of the novel concepts of the disclosure.

It is to be understood that both the foregoing general description and the following detailed description are exemplary and explanatory only and are not restrictive of the invention, as claimed.

DETAILED DESCRIPTION OF THE INVENTION

Various embodiments of the invention are now described in detail. As used in the description and throughout the claims, the meaning of "a", "an", and "the" includes plural reference unless the context clearly dictates otherwise. Also, as used in the description and throughout the claims, the meaning of "in" includes "in" and "on" unless the context clearly dictates otherwise. Additionally, some terms used in this specification are more specifically defined below.

DEFINITIONS

The terms used in this specification generally have their ordinary meanings in the art, within the context of the invention, and in the specific context where each term is used. Certain terms that are used to describe the invention are discussed below, or elsewhere in the specification, to provide additional guidance to the practitioner regarding the description of the invention. Synonyms for certain terms are provided. A recital of one or more synonyms does not exclude the use of other synonyms. The use of examples anywhere in this specification including examples of any terms discussed herein is illustrative only, and in no way limits the scope and meaning of the invention or of any exemplified term. The invention is not limited to the various embodiments given in this specification.

Unless otherwise defined, all technical and scientific terms used herein have the same meaning as commonly understood by one of ordinary skill in the art to which this invention pertains. In the case of conflict, the present document, including definitions will control.

"Around," "about" or "approximately" shall generally mean within 20 percent, within 10 percent, within 5, 4, 3, 2 or 1 percent of a given value or range. Numerical quantities given are approximate, meaning that the term "around," "about" or "approximately" can be inferred if not expressly stated.

The term "etanercept" or "etanercept monomer" or "monomer" is synonymous with Enbrel®. It refers to a polypeptide which is a dimeric fusion polypeptide consisting of the extracellular ligand-binding portion of the human 75 kilodalton (p75) tumor necrosis factor receptor (TNFR) linked to the Fc portion of human IgG1. It consists of 934 amino acids and has an apparent molecular weight of approximately 150 kilodaltons. For the purposes of the present application, the term "etanercept" also encompasses etanercept with minor modifications in the amino acid structure (including deletions, additions, and/or substitutions of amino acids) which do not significantly affect the function of the polypeptide. The term "etanercept" encompasses all forms and formulations of Enbrel®, including but not limited to concentrated formulations, injectable ready-to-use formulations; formulations reconstituted with water, alcohol, and/or other ingredients, and others.

The term "meglumine" refers to a compound with chemical formula $H_3NHCH_2(CHOH)_4CH_2OH$, also known as 1-Deoxy-1-methylaminosorbitol; N-Methyl-d-glucamine; and 1-Deoxy-1-methylamino-D-glucitol.

The terms "mannosylglycerate," "mannosyllactate," "mannosylglycolate", and "diglycerolphosphate" are well known in the art and have their commonly accepted meanings. The following references describe these compounds in some detail: Faria et al., *Carbohydrate Res.* 2008, 343: 3025-3033; Borges et al., *Extremophiles* 2002, 6: 209-216; Faria et al., *ChemBioChem* 2003, 4: 734-741; Sawangwan et al., *Biotechnol. J.* 2010, 5: 187-191; and Pais et al., *J. Mol. Biol.* 2009, 394: 237-250. The application incorporates by reference the description of these compounds contained in these references. The term "serine" refers to an amino acid whose codons are UCU, UCC, UCA, UCG, AGU, and AGC The term "proline" refers to an α-amino acid whose codons are CCU, CCC, CCA, and CCG.

The term "glutamate" refers to a carboxylate anion or salt of glutamic acid (Glu). For the purposes of this application, the term "glutamate" also encompasses glutamic acid itself.

The term "sugar" refers to monosaccharides, disaccharides, and polysaccharides. Examples of sugars include, but are not limited to, sucrose, glucose, dextrose, and others.

The term "polyol" refers to an alcohol containing multiple hydroxyl groups. Examples of polyols include, but are not limited to, mannitol, sorbitol, and others.

The term "metal ion" refers to a metal atom with a net positive or negative electric charge. For the purposes of the present application, the term "metal ion" also includes sources of metal ions, including but not limited to metal salts.

The term "long-term storage" is understood to mean that the pharmaceutical composition can be stored for three months or more, for six months or more, and preferably for one year or more. Long term storage is also understood to mean that the pharmaceutical composition is stored either as a liquid at 2-8° C., or is frozen, e.g., at −20° C., or colder. It is also contemplated that the composition can be frozen and thawed more than once.

The term "stable" or "stabilized" with respect to long-term storage is understood to mean that etanercept contained in the pharmaceutical compositions does not lose more than 20%, or more preferably 15%, or even more preferably 10%, and most preferably 5% of its activity relative to activity of the composition at the beginning of storage.

The term "mammal" includes, but is not limited to, a human.

The term "pharmaceutically acceptable carrier" refers to a non-toxic solid, semisolid or liquid filler, diluent, encapsulating material, formulation auxiliary, or excipient of any conventional type. A pharmaceutically acceptable carrier is non-toxic to recipients at the dosages and concentrations employed and is compatible with other ingredients of the formulation.

The term "composition" refers to a mixture that usually contains a carrier, such as a pharmaceutically acceptable carrier or excipient that is conventional in the art and which is suitable for administration into a subject for therapeutic, diagnostic, or prophylactic purposes. It may include a cell culture in which the polypeptide or polynucleotide is present in the cells or in the culture medium. For example, compositions for oral administration can form solutions, suspensions, tablets, pills, capsules, sustained release formulations, oral rinses or powders.

The terms "pharmaceutical composition" and "formulation" are used interchangeably.

The term "treatment" refers to any administration or application of remedies for disease in a mammal and includes inhibiting the disease, arresting its development, relieving the disease, for example, by causing regression, or restoring or repairing a lost, missing, or defective function; or stimulating an inefficient process. The term includes obtaining a desired pharmacologic and/or physiologic effect, covering any treatment of a pathological condition or disorder in a mammal. The effect may be prophylactic in terms of completely or partially preventing a disorder or symptom thereof and/or may be therapeutic in terms of a partial or complete cure for a disorder and/or adverse affect attributable to the disorder. It includes (1) preventing the disorder from occurring or recurring in a subject who may be predisposed to the disorder but is not yet symptomatic, (2) inhibiting the disorder, such as arresting its development, (3) stopping or terminating the disorder or at least its associated symptoms, so that the host no longer suffers from the disorder or its symptoms, such as causing regression of the disorder or its symptoms, for example, by restoring or repairing a lost, missing or defective function, or stimulating an inefficient process, or (4) relieving, alleviating or ameliorating the disorder, or symptoms associated therewith, where ameliorating is used in a broad sense to refer to at least a reduction in the magnitude of a parameter, such as inflammation, pain and/or tumor size.

The term "disease" refers to any condition, infection, disorder or syndrome that requires medical intervention or for which medical intervention is desirable. Such medical intervention can include treatment, diagnosis and/or prevention.

The term "therapeutically effective amount" refers to an amount which, when administered to a living subject, achieves a desired effect on the living subject. For example, an effective amount of the polypeptide of the invention for administration to the living subject is an amount that prevents and/or treats an integrin $\alpha v \beta 3$-mediated disease. The exact amount will depend on the purpose of the treatment, and will be ascertainable by one skilled in the art using known techniques. As is known in the art, adjustments for systemic versus localized delivery, age, body weight, general health, sex, diet, time of administration, drug interaction and the severity of the condition may be necessary, and will be ascertainable with routine experimentation by those skilled in the art.

EMBODIMENTS OF THE INVENTION

When pharmaceutical compositions containing etanercept (Enbrel®), including aqueous and lyophilized formulations of etanercept are stored on a long term basis, the activity of etanercept can be lost or decreased due to instability of the etanercept monomer via aggregation and/or degradation including formation of fragments and oligomers. Thus, the present invention provides several embodiments of aqueous formulations of etanercept that allow stable long-term storage of etanercept, so that etanercept is stable over the course of storage either in liquid or frozen states. The provided formulations include, but are not limited to formulations which do not contain arginine and do not require any extra steps such as rehydrating.

These embodiments are explained in a greater detail below.

Etanercept

All of the compositions of the present invention comprise etanercept (Enbrel®). As explained in the Background section of this application, etanercept is a dimeric fusion polypeptide consisting of the extracellular ligand-binding portion of the human 75 kilodalton (p75) tumor necrosis factor receptor (TNFR) linked to the Fc portion of human IgG1. Etanercept consists of 934 amino acids. The Fc component of etanercept contains the constant heavy 2 (CH2) domain, the constant heavy 3 (CH3) domain and hinge region of human IgG1. An Fc domain can contain one or all of the domains described above.

Etanercept suitable for storage in the present pharmaceutical composition can be produced by living host cells that express etanercept, such as hybridomas in the case of antibodies, or host cells that that have been genetically engineered to produce the polypeptide in the case of fusion polypeptides or antibodies. Methods of genetically engineering cells to produce polypeptides are well known in the art. See, e.g., Ausubel et al., eds. (1990), Current Protocols in Molecular Biology (Wiley, New York). Such methods include introducing nucleic acids that encode and allow expression of the polypeptide into living host cells. These host cells can be bacterial cells, fungal cells, or, preferably, animal cells grown in culture. Bacterial host cells include, but are not limited to, *Escherichia coli* cells. Examples of suitable *E. coli* strains include: HB101, DH5.alpha, GM2929, JM109, KW251, NM538, NM539, and any *E. coli* strain that fails to cleave foreign DNA. Fungal host cells that can be used include, but are not limited to, *Saccharomyces cerevisiae, Pichia pastoris* and *Aspergillus* cells. A few examples of animal cell lines that can be used are CHO, VERO, BHK, HeLa, Cos, MDCK, 293, 3T3, and W138. New animal cell lines can be established using methods well know by those skilled in the art (e.g., by transformation, viral infection, and/or selection). Optionally, etanercept can be secreted by the host cells into the medium.

Purification of the expressed etanercept can be performed by any standard method. When etanercept is produced intracellularly, the particulate debris is removed, for example, by centrifugation or ultrafiltration. When etanercept is secreted into the medium, supernatants from such expression systems can be first concentrated using standard polypeptide concentration filters. Protease inhibitors can also be added to inhibit proteolysis and antibiotics can be included to prevent the growth of microorganisms.

Etanercept can be purified using, for example, hydroxyapatite chromatography, gel electrophoresis, dialysis, and affinity chromatography, and any combination of known or yet to be discovered purification techniques, including but not limited to Protein A chromatography, fractionation on an ion-exchange column, ethanol precipitation, reverse phase HPLC, chromatography on silica, chromatography on heparin SEPHAROSET®, an anion or cation exchange resin chromatography (such as a polyaspartic acid column), chromatofocusing, SDS-PAGE, and ammonium sulfate precipitation.

I. Etanercept Stabilized with Serine, Proline or Glutamate

In one embodiment, the invention provides a stable aqueous pharmaceutical composition comprising etanercept and a stabilizer to inhibit instability, aggregation and/or fragmentation of the etanercept, wherein the stabilizer comprises a compound selected from the group consisting of serine, proline and glutamate. In a preferred embodiment, the stabilizer comprises glutamate.

Without intending to be bound to any particular theory of the invention, it is believed that serine, proline and glutamate act as stabilizers to reduce etanercept's tendency to associate in undesired ternary or quaternary complexes, and therefore to reduce aggregation of etanercept. The reduction in aggregation is believed to last for a long period of time, e.g., two years or more. It is believed that serine, proline and glutamate are able to stabilize aqueous pharmaceutical compositions containing etanercept because they are excluded from the surface of the protein, resulting in net conformation stabilization. The stabilizing effects of serine, proline and/or glutamate include but are not limited to the benefits of reduced aggregation of the etanercept monomer in formulations containing the monomer.

The pharmaceutical compositions of the invention may be prepared by combining a purified etanercept and a stabilizer. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In a preferred embodiment, the concentration of the serine, proline or glutamate stabilizer in the provided formulations is preferably up to about 150 mM.

Serine, proline and glutamate are available from commercial suppliers.

In an embodiment in which the stabilizer comprises glutamate, a formulation of the invention can comprise about 25 to about 50 mg/ml of etanercept; up to 150 mM glutamate; less than about 6 wt. % sucrose; optionally up to about 100 mM NaCl; about 1 to about 30 mM sodium phosphate, and wherein the formulation has pH 6.0 to about pH 7.0 and more preferably about 6.0 to about 6.6, and most preferably between about 6.3 to about 6.5.

In an embodiment in which the stabilizer comprises serine, a formulation of the invention can comprise about 25 to about 50 mg/ml of etanercept; less than about 150 mM serine; about 0.5 to about 3 wt. % sucrose; about 1 to about 30 mM sodium phosphate, and wherein the formulation has pH 6.0 to about pH 7.0 and more preferably about 6.0 to about 6.6, and most preferably between about 6.3 to about 6.5.

In an embodiment in which the stabilizer comprises proline, a formulation of the invention can comprise about 25 to about 50 mg/ml of etanercept; less than about 150 mM proline; about 0.5 to about 3 wt. % sucrose; about 1 to about 30 mM sodium phosphate, about 15 to about 100 mM NaCl; and wherein the formulation has pH 6.0 to about pH 7.0 and more preferably about 6.0 to about 6.6, and most preferably between about 6.3 to about 6.5.

Etanercept formulations according to the present invention comprising serine, proline or glutamate are preferably characterized by an SEC analysis at $T_2$ of: about 80 to about 95 wt. % monomer content; less than about 4 wt. % aggregate(s) content; and less than about 8 wt. % fragment 3 content.

In formulations containing serine, proline or glutamate for stabilization, the formulations are more preferably characterized by:
  (a) an SEC analysis at $T_4$ of greater than about 90, 91, 92, 93, 94, 95, 96, or 97 wt. % monomer content; and less than about 3, 2 or 1 wt. % aggregate(s) content; and
  (b) an HIC analysis at $T_2$ wherein the amount of the composition represented by peak 1 of the HIC chromatogram is less than about 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than about 20, 19, 18, 17, 16, 15, 14, or 13 wt. %; and
  (c) an HIC analysis at $T_4$ wherein the amount of the composition represented by peak 1 of the HIC chromatogram is less than about 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than 20, 19, 18, 17, 16, 15, 14 or 13 wt. %.

The terms "SEC", "$T_2$," "$T_4$," "HIC" "monomer content" "aggregate(s)" and "fragment 3" "peak 1," "peak 2," and "peak 3," are defined in the examples below.

In particularly preferred formulations containing serine, proline or glutamate for stabilization preferably are characterized by having an HIC analysis at $T_4$ or $T_2$ wherein the amount of the composition represented by peak 1 of the HIC chromatogram is less than about 1%; the amount of the composition represented by peak 2 of the HIC chromatogram is greater than about 95 wt. %, and most preferably greater than about 99 wt. %; and the amount of the composition represented by peak 3 of the HIC chromatogram is less than about 1 wt. %.

A further preferred formulation using serine, proline and/or glutamate for stabilization of etanercept comprises about 50 mg/ml etanercept; less than about 150 mM serine, proline or glutamate, and most preferably glutamate; about 0 to 3% sucrose; about 1 to 30 mM phosphate buffer, and having a pH of about 6.0 to 6.6; and characterized by: an SEC analysis at $T_4$ of greater than about 97 wt. % monomer content and less than about 1 wt. % aggregate(s) content; an HIC analysis at $T_2$ wherein the amount of the composition represented by peak 1 of the HIC chromatogram is less than about 3 wt. %; the amount of the composition represented by peak 2 of the HIC chromatogram is greater than about 82 wt. %; and the amount of the composition represented by peak 3 of the HIC chromatogram is less than about 15 wt. %; and an HIC analysis at $T_4$ wherein the amount of the composition represented by peak 1 of the HIC chromatogram is less than about 2 wt. %; the amount of the composition represented by peak 2 of the HIC chromatogram is greater than about 84 wt. %; and the amount of the composition represented by peak 3 of the HIC chromatogram is less than about 13 wt. %.

A further preferred glutamate stabilized etanercept formulation comprises: about 50 mg/ml etanercept; about 120 mM glutamate; about 1% sucrose, and about 25 mM phosphate; having a pH of about 6.3 to about 6.5, and exhibiting the SEC and HIC analytical characteristics referenced above.

Although the invention does not exclude the use of arginine, the etanercept formulations comprising serine, proline and/or glutamate for stabilization according to the present invention are preferably free or essentially free of arginine.

II. Etanercept Stabilized with a Metal Ion

In another embodiment, the invention provides a stabilized aqueous pharmaceutical composition comprising etanercept and a stabilizer to inhibit instability, aggregation and/or fragmentation of the etanercept, wherein the stabilizer comprises a stabilizing metal ion.

It is believed that metal ions such as calcium, magnesium, and zinc reduce etanercept's tendency to associate in undesired ternary or quaternary complexes, and therefore, reduce aggregation of etanercept. The reduction in aggregation is believed to last for a long period of time, e.g., two years or more. Without wishing to be bound to a particular theory, it is believed that metal ions are able to stabilize aqueous pharmaceutical compositions containing etanercept because the metal can bind to the native state, where the right geometry of ligands occurs. In doing so, there is a net stabilization of the native state. Once the protein unfolds, the binding site is lost, and the denatured state in relatively unaffected in terms of free energy. The result is a net stabilization of the conformation, leading to improved long-term storage. In addition, metal biding may also improve the colloidal stability of the protein, leading to decreased aggregation and increased solubility. The stabilization effects of metal ion are may not be limited to reduction in aggregates but may also address other aspects of instability of the etanercept monomer in the formulation.

In a preferred embodiment, the metal ion is selected from the group consisting of calcium, magnesium, zinc, and combinations thereof. In an even more preferred embodiment, calcium, magnesium, and zinc are provided as calcium chloride, magnesium chloride and zinc chloride, respectively.

The pharmaceutical compositions of the invention may be prepared by combining, a purified etanercept and a metal ion. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In a preferred embodiment, the concentration of the metal ion in the provided formulations is preferably between about 1 mM to 0.5 M, more preferably about 1 mM to about 100 mM, more preferably about 2 mM to about 20 mM, and yet more preferably about 2 to 10 mM.

Sources of metal ions are available from commercial suppliers.

In an embodiment using calcium chloride for stabilization, an etanercept formulation of the invention comprises about 25 to about 50 mg/ml of etanercept; up to about 5 mM calcium chloride; optionally about 0.5 to 6 wt. % sucrose or trehalose; optionally about 0 to 100 mM NaCl; optionally up to about 10 mM xylitol; about 1 to about 30 mM sodium phosphate; wherein the composition has a pH of about 6.0 to about pH 7.0, and more preferably about 6.0 to about 6.6 and most preferably about 6.3 to about 6.5.

In an embodiment using magnesium chloride for stabilization, an etanercept formulation of the invention comprises about 25 to about 50 mg/ml of etanercept; about 1 mM to about 20 mM magnesium chloride; optionally up to about 6 wt. % sucrose; about 25 to 150 mM NaCl; about 1 to about 30 mM sodium phosphate; wherein the composition has a pH of about 6.0 to about pH 7.0, and more preferably about 6.0 to about 6.6 and most preferably about 6.3 to about 6.5.

Compositions stabilized with metal ions are preferably characterized as having an SEC analysis at $T_2$ of: about 80 wt. % to about 95 wt. % monomer content; an SEC analysis at $T_2$ of aggregate(s) content of less than about 4 wt. %; and an SEC analysis at $T_2$ of fragment 3 content of less than about 8 wt. %.

More preferably the etanercept formulations containing a stabilizing metal ion according to the invention are characterized by:

(a) an SEC analysis at $T_4$ of greater than about 90, 91, 92, 93, 94, 95, 96, or 97 wt. % monomer content; and less than about 3, 2 or 1 wt. % aggregate(s) content; and (b) an HIC analysis at $T_2$ wherein the amount of the composition represented by peak 1 of the HIC chromatogram is less than about 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than about 20, 19, 18, 17, 16, 15, 14, or 13 wt. %; and (c) an HIC analysis at $T_4$ wherein the amount of the composition represented by peak 1 of the HIC chromatogram is less than about 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than 20, 19, 18, 17, 16, 15, 14 or 13 wt. %.

The etanercept formulations of the present invention containing metal ion for stabilization are more preferably characterized by having an HIC analysis at $T_4$ or $T_2$ wherein the amount of the composition represented by peak 1 of the HIC chromatogram is less than about 1%; the amount of the composition represented by peak 2 of the HIC chromatogram is greater than about 95 wt. % and most preferably greater than about 99 wt. %; and the amount of the composition represented by peak 3 of the HIC chromatogram is less than about 1 wt. %.

The terms "SEC", "$T_2$," "$T_4$," "HIC" "monomer content" "aggregate(s)" and "fragment 3" "peak 1," "peak 2," and "peak 3," are defined in the examples below.

Preferred etanercept formulations stabilized with calcium chloride comprise: about 50 mg/ml etanercept; 1 to 5 mM calcium chloride; about 1 to 30 mM sodium phosphate; about 0 to 100 mM NaCl; about 0.5 to 5% sucrose or trehalose or combination thereof; and wherein the composition has a pH of about 6.0 to 6.6 and characterized by: an SEC analysis at $T_4$ of greater than about 97 wt. % monomer content and less than about 1 wt. % aggregate(s) content; an HIC analysis at $T_2$ wherein the amount of the composition represented by peak 1 of the HIC chromatogram is less than about 4 wt. %; the amount of the composition represented by peak 2 of the HIC chromatogram is greater than about 82 wt. %; and the amount of the composition represented by peak 3 of the HIC chromatogram is less than about 15 wt. %; and an HIC analysis at $T_4$ wherein the amount of the composition represented by peak 1 of the HIC chromatogram is less than about 2 wt. %; the amount of the composition represented by peak 2 of the HIC chromatogram is greater than about 85 wt. %; and the amount of the composition represented by peak 3 of the HIC chromatogram is less than about 13 wt. %.

Preferred etanercept formulations stabilized with magnesium chloride comprise: about 1 mM to about 20 mM magnesium chloride; optionally up to about 6 wt. % sucrose; about 25 to 150 mM NaCl; about 1 to about 30 mM sodium phosphate; wherein the composition has a pH of about 6.0 to 6.6; and wherein the composition is characterized by: an SEC analysis at $T_4$ of greater than about 97 wt. % monomer content and less than about 1 wt. % aggregate(s) content; an HIC analysis at $T_2$ wherein the amount of the composition represented by peak 1 of the HIC chromatogram is less than about 4 wt. %; the amount of the composition represented by peak 2 of the HIC chromatogram is greater than about 85 wt. %; and the amount of the composition represented by peak 3 of the HIC chromatogram is less than about 14 wt. %; and an HIC analysis at $T_4$ wherein the amount of the composition represented by peak 1 of the HIC chromatogram is less than about 2 wt. %; the amount of the composition represented by peak 2 of the HIC chromatogram is greater than about 85 wt. %; and the amount of the composition represented by peak 3 of the HIC chromatogram is less than about 14 wt. %.

In particularly preferred embodiments of the invention using calcium chloride for stabilization, a stabilized etanercept formulation having the analytical properties referenced above comprises: about 50 mg/ml of etanercept; about 2 mM calcium chloride; about 15 mM sodium phosphate; about 75 mM sodium chloride; and about 3 wt. % sucrose; wherein the formulation has a pH of about 6.3 to 6.5.

In a further preferred embodiment of the invention using magnesium chloride for stabilization, a stabilized etanercept formulation having the analytical properties referenced above comprises: about 50 mg/ml of etanercept; about 10 mM magnesium chloride; about 15 mM sodium phosphate; about 75 mM sodium chloride; and about 3 wt. % sucrose; and having a pH of about 6.3 to 6.5.

The terms "SEC", "$T_2$," "$T_4$" "HIC" "monomer content" "aggregate(s)" and "fragment 3" "peak 1," "peak 2," and "peak 3," are defined in the examples below.

Although the use of stabilizing metal ions according to the invention does not exclude the use of arginine, the etanercept formulations comprising metal ion for stabilization according to the present invention are preferably free or essentially free of arginine.

III. Etanercept Stabilized with an Ionic Polyol Derivative Excipient

In another embodiment, the invention provides a stable aqueous formulation comprising etanercept and an ionic polyol derivative excipient, wherein said excipient is selected from the group consisting of meglumine (N-methyl-D-glucamine), mannosylglycerate, glucosylglycerate, mannosyllactate, mannosylglycolate, and diglycerolphosphate.

Preferably, in this embodiment or aspect, the invention is an aqueous stabilized formulation of etanercept comprising: etanercept; and stabilizing ingredients to retard instability, aggregation and fragmentation of the etanercept in the formulation, said stabilizing ingredients being comprised of (a) meglumine; or (b) meglumine in combination with sucrose; or (c) meglumine in combination with sodium chloride; or (d) meglumine in combination with sodium chloride and sucrose.

Meglumine is commonly used as a small molecule excipient. We have now surprisingly found that meglumine is also able to stabilize aqueous pharmaceutical compositions containing a large protein, such as etanercept.

It is believed that meglumine reduces etanercept's tendency to associate in undesired ternary or quaternary complexes, and therefore, reduces aggregation of etanercept. The reduction in aggregation is believed to last for a long period of time, e.g., two years or more. Without wishing to be bound to a particular theory, it is believed that meglumine is able to stabilize aqueous pharmaceutical compositions containing etanercept by a combination of three different mechanisms. First, meglumine can act as an excluded solute in the same way mannitol, sucrose, and sorbitol increase conformational stability. Second, charged solutes can alter the colloidal stability, thereby reducing the propensity to self-associate, thereby slowing aggregation. Third, these ionic polyol derivatives, being charged near neutral pH, can act as salting-in agents, as arginine does, potentially resolubilizing aggregates. The stabilizing effects of meglumine are not limited to reduction in aggregates but may involve other aspects of stabilization of the etanercept monomer in a formulation containing the monomer.

The pharmaceutical compositions of the invention may be prepared by combining, a purified etanercept and the ionic polyol derivative, preferably meglumine. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In a preferred embodiment, the concentration of meglumine in the provided formulations is preferably between about 0.1% (w/v) to 40% (w/v), more preferably about 1% to about 20%, more preferably about 2% to about 10%, even more preferably about 2% to about 5%.

Meglumine is available from commercial suppliers.

A preferred embodiment comprises about 25 to about 75 mg/ml etanercept, about 1-30 mM of sodium phosphate; up to about 10% meglumine; optionally up to about 5 wt. % sucrose; and optionally up to about 100 mM sodium chloride, wherein the composition has a pH of about 6.0 to 7.0, and preferably about 6.0 to about 6.6 and most preferably about 6.3 to about 6.5.

A meglumine stabilized etanercept composition is preferably characterized by SEC analysis at $T_2$ in which: the monomer content is greater than about 85 wt. %;

aggregate(s) content is less than about 3 wt. %; and fragment 3 content is less than about 8 wt. %.

A more preferred formulation of etanercept wherein an ionic polyol derivative such as meglumine is present for stabilization is one that is characterized by:

(a) an SEC analysis at $T_4$ of greater than about 90, 91, 92, 93, 94, 95, 96, or 97 wt. % monomer content; and less than about 3, 2 or 1 wt. % aggregate(s) content; and (b) an HIC analysis at $T_2$ wherein the amount of the composition represented by peak 1 of the HIC chromatogram is less than about 4, 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than about 20, 19, 18, 17, 16, 15, 14, or 13 wt. %; and (c) an HIC analysis at $T_4$ wherein the amount of the composition represented by peak 1 of the HIC chromatogram is less than about 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than 20, 19, 18, 17, 16, 15, 14 or 13 wt. %.

A particularly preferred etanercept formulation stabilized with meglumine is characterized by HIC analysis at $T_4$ or $T_2$ wherein the amount of the composition represented by peak 1 of the HIC chromatogram is less than about 1%; the amount of the composition represented by peak 2 of the HIC chromatogram is greater than about 99 wt. %; and the amount of the composition represented by peak 3 of the HIC chromatogram is less than about 1 wt. %.

The terms "SEC", "$T_2$," "$T_4$," "HIC" "monomer content" "aggregate(s)" and "fragment 3" "peak 1," "peak 2," and "peak 3," are defined in the examples below.

In other embodiments meglumine can be replaced with another ionic polyol derivative of sorbitol, glycerol or mannitol, such as mannosylglycerate, glucosylglycerate, mannosyllactate, mannosylglycolate, and diglycerolphosphate (at about 0.1% to about 40%) in the formulation.

A preferred meglumine-stabilized etanercept formulation free of arginine and exhibiting analytical properties as described above comprises about 25 to about 75 mg/ml etanercept; about 0.5 wt. % meglumine; about 25 mM phosphate; about 1% sucrose; and about 100 mM sodium chloride.

A further preferred meglumine-stabilized etanercept formulation free of arginine and exhibiting analytical properties as described above comprises about 50 mg/ml etanercept; about 5 wt. % meglumine; about 25 mM phosphate.

Although the invention does not exclude the use of arginine, the etanercept formulations comprising ionic polyol derivatives such as meglumine for stabilization according to the present invention are preferably free or essentially free of arginine.

IV. Etanercept Stabilized with a Combination of a Sugar and a Polyol

In yet another embodiment, the invention provides a stable aqueous formulation comprising etanercept, a sugar and a polyol.

It is believed that a combination of a sugar and a polyol reduces etanercept's tendency to associate in undesired ternary or quaternary complexes, and therefore, reduces aggregation of etanercept. The reduction in aggregation is believed to last for a long period of time, e.g., two years or more. Thus, a combination of a sugar and a polyol is believed to be able to stabilize aqueous pharmaceutical compositions containing etanercept. Without wishing to be bound to a particular theory, the combination of a sugar and a polyol is believed to be synergistic for the purposes of stabilizing etanercept because even though excluded solutes are, on average, residing in the bulk, rather than on the surface of the protein, the fact is that there will be interactions between sugars/polyols and the protein. Those interactions will likely differ between sugars and smaller polyols. In addition, at high concentrations, the two additives will alter the thermodynamic activity of the other, thereby leading to solution behavior that will be different than what would be observed for each individual component. As discussed further below, amines can be substituted for the polyol.

The pharmaceutical compositions of the invention may be prepared by combining a purified etanercept, a sugar, and a polyol. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In some embodiments, a sugar and a polyol may act in concert, in the same way two metals form an alloy with properties not exhibited by either metal. It should be understood that the same approach would lead one to use amino acids, such as proline, serine, or glutamate along with a sugar to achieve a stability profile better than either excipient could provide on its own. A preferred ratio of a sugar to a polyol (or amino acid) in the alloy is believed to be between 5:1 to 1:5.

The most preferred sugars are believed to be sucrose, trehalose, lactose, raffinose, and maltose.

The most preferred polyols are believed to be sorbitol, mannitol, glycerol, and propylene glycol.

The preferred amino acids are believed to be proline, serine, threonine, and glutamate.

In a preferred embodiment, the concentration of a sugar in the provided formulations is preferably between about 0.1% (w/v) to 40%, more preferably about 1% to about 20%, more preferably about 2% to about 10%, and yet more preferably about 5% to 9%.

In a preferred embodiment, the concentration of a polyol in the provided formulations is preferably between about 0.1% to 30%, more preferably about 1% to about 10%, and yet more preferably about 2% to about 5%.

Sugars and polyols are available from commercial suppliers.

In one embodiment, a formulation of the invention comprises about 25 to about 75 mg/ml of etanercept; about 1% to about 10% sucrose; about 1% to about 5% mannitol; about 10 mM to about 50 mM sodium phosphate; and about 0 mM to about 100 mM NaCl, at about pH 6.3 to about pH 7.0.

In another embodiment, sucrose can be replaced with another sugar such as trehalose (at about 1% to about 10%) in the formulation. In yet another embodiment, mannitol can be replaced with another polyol such as sorbitol (at about 1% to about 5%) in the formulation.

Although the invention does not exclude the use of arginine the etanercept formulations comprising sugar and polyol (or amino acid) for stabilization are preferably free or essentially free of arginine.

V. Etanercept Stabilized with Xylitol

In yet another embodiment, the invention provides a stabilized aqueous pharmaceutical composition comprising etanercept and a stabilizer to inhibit instability, aggregation and/or fragmentation of the etanercept, wherein the stabilizer comprises xylitol or a combination of xylitol and meglumine.

Without wishing to be bound to any particular theory, It is believed that xylitol reduces etanercept's tendency to associate in undesired ternary or quaternary complexes, and therefore, reduces aggregation of etanercept. The reduction in aggregation is believed to last for a long period of time, e.g., two years or more. The stabilizing effects of xylitol are not limited to reduction in aggregates but may involve other aspects of stabilization of the etanercept monomer in a formulation containing the monomer.

A preferred stabilized etanercept formulation incorporating xylitol for stabilization is one in which stabilization is provided by a combination of xylitol and meglumine.

The pharmaceutical compositions of the invention may be prepared by combining, a purified etanercept and xylitol, or xylitol in combination with meglumine. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

Xylitol stabilized etanercept formulations of the invention can comprise about 25 to 75 mg/ml of etanercept; about 1-10 wt. % xylitol; about 1 to 30 mM sodium phosphate; optionally up to about 5 wt. % meglumine; optionally up to about 5 mM NaCl; and optionally up to about 5 wt. % sucrose.

Xylitol stabilized etanercept formulations which additionally contain meglumine, sodium chloride and sucrose can comprise, in addition to xylitol, comprise about 1-3 mM NaCl; about 1 to 5 wt. % sucrose; and meglumine in an amount of about 1-5 wt. % of the composition.

In a further embodiment, xylitol stabilized etanercept formulations can comprise about 25 to about 75 mg/ml of etanercept; and a stabilizer to inhibit instability, aggregation and/or fragmentation of the etanercept, wherein the stabilizer is xylitol in an amount constituting up to about 10 wt. % of the composition, and wherein the composition is characterized by an SEC analysis at $T_2$ of: about 80 wt. % to about 95 wt. % monomer content; an SEC analysis at $T_2$ of aggregate(s) content of less than about 4 wt. % and preferably less than about 3 wt. %; and an SEC analysis at $T_2$ of fragment 3 content of less than about 8 wt. % and preferably less than about 6 wt. %; wherein the composition has a pH of about 6.0 to about pH 7.0, and more preferably about 6.0 to about 6.6 and most preferably about 6.3 to about 6.5.

In stabilized etanercept formulations such as those referenced above containing xylitol or xylitol in combination with meglumine, the formulations are more preferably characterized by:
(a) an SEC analysis at $T_4$ of greater than about 90, 91, 92, 93, 94, 95, 96, or 97 wt. % monomer content; and less than about 3, 2 or 1 wt. % aggregate(s) content; and
(b) an HIC analysis at $T_2$ wherein the amount of the composition represented by peak 1 of the HIC chromatogram is less than about 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than about 20, 19, 18, 17, 16, 15, 14, or 13 wt. %; and
(c) an HIC analysis at $T_4$ wherein the amount of the composition represented by peak 1 of the HIC chromatogram is less than about 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than 20, 19, 18, 17, 16, 15, 14 or 13 wt. %.

The terms "SEC", "$T_2$," "$T_4$," "HIC" "monomer content" "aggregate(s)" and "fragment 3" "peak 1," "peak 2," and "peak 3," are defined in the examples below.

Particularly preferred formulations containing xylitol, or xylitol in combination with meglumine are characterized by having an HIC analysis at $T_4$ or $T_2$ wherein the amount of the composition represented by peak 1 of the HIC chromatogram is less than about 1%; the amount of the composition represented by peak 2 of the HIC chromatogram is greater than about 95 wt. % and preferably greater than about 99 wt. %; and the amount of the composition represented by peak 3 of the HIC chromatogram is less than about 1 wt. %. Specific xylitol-stabilized formulations are provided in the detailed examples.

Although the invention does not exclude the use of arginine, the etanercept formulations comprising xylitol for stabilization according to the present invention are free or essentially free of arginine.

VI. Etanercept Formulations Stabilized with NaCl

In yet another embodiment, the invention provides an aqueous etanercept formulation stabilized to reduce instability, aggregation and/or fragmentation of the etanercept, said formulation comprising about 25 to about 75 mg/ml of etanercept and one or more stabilizers, wherein the stabilizers are selected from the group consisting of (i) sodium chloride and (ii) sodium chloride in combination with sucrose or trehalose; and (iii) a combination of sodium chloride, sucrose and trehalose.

The pharmaceutical compositions of the invention may be prepared by combining, a purified etanercept and sodium chloride, optionally with sucrose and/or trehalose. Further, a buffer, a tonicity modifier and an additional excipient and other commonly used inactive ingredients can be added as needed. For simplicity, these are discussed more fully later in the specification. A person of ordinary skill in the art will understand that the combining of the various components to be included in the composition can be done in any appropriate order. For example, the buffer can be added first, middle or last, and the tonicity modifier can also be added first, middle or last. A person of ordinary skill in the art will also understand that some of these chemicals can be incompatible in certain combinations, and accordingly, are easily substituted with different chemicals that have similar properties but are compatible in the relevant mixture.

In an embodiment using sodium chloride for stabilization, an etanercept formulation of the invention comprises about 25 to 75 mg/ml etanercept, up to about 150 mM of sodium chloride, about 1 to about 30 mM sodium phosphate; and about 0 to 5 wt. % sucrose or trehalose or combination thereof; wherein the composition has a pH of about 6.0 to about pH 7.0, and more preferably about 6.0 to about 6.6 and most preferably about 6.3 to about 6.5.

The sodium chloride stabilized composition is preferably characterized by SEC analysis at $T_2$ in which: monomer content is greater than about 80 wt. %; aggregate(s) content is less than about 3 wt. %, and fragment 3 content is about 8 wt. %.

The sodium chloride-stabilized etanercept composition is preferably characterized by:
(a) an SEC analysis at $T_4$ of greater than about 90, 91, 92, 93, 94, 95, 96, or 97 wt. % monomer content; and less than about 3, 2 or 1 wt. % aggregate(s) content; and
(b) an HIC analysis at $T_2$ wherein the amount of the composition represented by peak 1 of the HIC chromatogram is less than about 4, 3, 2 or 1 wt. %; the amount of the composition represented by peak 2 of the HIC chromatogram is greater than 80, 81, 82, 83, 84 85 or 86 wt. %; and the amount of the composition represented by peak 3 of the HIC chromatogram is less than about 20, 19, 18, 17, 16, 15, 14, or 13 wt. %; and
(c) an HIC analysis at $T_4$ wherein the amount of the composition represented by peak 1 of the HIC chromatogram is less than about 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than 20, 19, 18, 17, 16, 15, 14 or 13 wt. %.

In a further embodiment, preferred composition using sodium chloride for stabilization comprise up to about 150 mM sodium chloride, about 1 to 30 mM sodium phosphate, and about 0-5 wt. % sucrose or trehalose, or combination of sucrose and trehalose and having a pH of about 6.0 to 6.6; and characterized by: an SEC analysis at $T_4$ of greater than about 95 wt. % monomer content and less than about 1 wt. % aggregate(s) content; an HIC analysis at $T_2$ wherein the amount of the composition represented by peak 1 of the HIC chromatogram is less than or equal to about 3 wt. %; the amount of the composition represented by peak 2 of the HIC chromatogram is greater than about 82 wt. %; and the amount of the composition represented by peak 3 of the HIC chromatogram is less than about 15 wt. %; and an HIC analysis at $T_4$ wherein the amount of the composition represented by peak 1 of the HIC chromatogram is less than about 2 wt. %; the amount of the composition represented by peak 2 of the HIC chromatogram is greater than about 84 wt. %; and the amount of the composition represented by peak 3 of the HIC chromatogram is less than or equal to about 14 wt. %.

Particularly preferred compositions in terms of reduced aggregates and fragments are those in which the sodium chloride stabilized etanercept formulations exhibit HIC analysis at $T_4$ or $T_2$ wherein the amount of the composition represented by peak 1 of the HIC chromatogram is less than about 1%; the amount of the composition represented by peak 2 of the HIC chromatogram is greater than about 95 wt. % and preferably greater than about 99 wt. %; and the amount of the composition represented by peak 3 of the HIC chromatogram is less than about 1 wt. %.

In a further embodiment of the invention, an NaCl stabilized etanercept formulation contains up to about 5 mM arginine.

In the above-referenced NaCl stabilized etanercept formulations, the terms "SEC", "$T_2$" "$T_4$" "HIC" "monomer content" "aggregate(s)" and "fragment 3" "peak 1," "peak 2," and "peak 3," are defined in the examples below.

Additional Components of the Provided Pharmaceutical Compositions

The formulations of the invention may also include buffers, tonicity modifiers, excipients, pharmaceutically acceptable carriers and other commonly used inactive ingredients of the pharmaceutical compositions. For simplicity, these are discussed more fully later in the application.

Buffers maintain pH in a desired range. Suitable buffers include histidine, potassium phosphate, sodium or potassium citrate, maleic acid, ammonium acetate, tris-(hydroxymethyl)-aminomethane (tris), various forms of acetate and diethanolamine. The concentration of the buffer in the formulation is preferably between about 1 mM to about 1M, and more preferably about 10 mM to about 200 mM. Buffers are well known in the art and are manufactured by known methods and available from commercial suppliers.

Examples of suitable buffers are phosphate, histidine, citrate, maleate, tartrate, succinate, acetate, tris-(hydroxymethyl)-aminomethane (tris), bicarbonate.

In a preferred embodiment, the buffer is sodium phosphate.

In a preferred embodiment, the pH of the pharmaceutical composition is at or near physiological levels. Thus, preferably, the pH of the provided compositions is between about 5.8 and about 8.4; and even more preferably, between about 6.2 and about 7.4. A person of ordinary skill in the art will understand that the pH can be adjusted as necessary to maximize stability and solubility of etanercept in a particular formulation. Thus, etanercept formulations at a pH outside of physiological ranges, yet tolerable to the patient, are also within the scope of the invention.

A tonicity modifier is a molecule that contributes to the osmolality of a solution. The osmolality of a pharmaceutical composition is preferably adjusted to maximize the active ingredient's stability and/or to minimize discomfort to the patient upon administration. It is generally preferred that a pharmaceutical composition be isotonic with serum, i.e., having the same or similar osmolality, which is achieved by addition of a tonicity modifier.

In a preferred embodiment, the osmolality of the provided formulations is from about 180 to about 420 mOsM. However, it is to be understood that the osmolality can be either higher or lower as specific conditions require.

Examples of tonicity modifiers suitable for modifying osmolality include, but are not limited to amino acids (not including arginine) (e.g., cysteine, histidine and glycine), salts (e.g., sodium chloride, potassium chloride and sodium citrate) and/or saccharides (e.g., sucrose, glucose and mannitol).

Preferred tonicity modifiers are glycine, alanine, sodium chloride, potassium chloride, and sodium sulfate.

In a preferred embodiment, the concentration of the tonicity modifier in the formulation is preferably between about 1 mM to about 1 M, more preferably about 10 mM to about 200 mM. Tonicity modifiers are well known in the art and are manufactured by known methods and available from commercial suppliers.

Excipients, also referred to as chemical additives, co-solutes, or co-solvents, that stabilize the polypeptide while in solution (also in dried or frozen forms) can also be added to a pharmaceutical composition. Excipients are well known in the art and are manufactured by known methods and available from commercial suppliers.

Examples of suitable excipients include but are not limited to sugars/polyols such as: sucrose, lactose, glycerol, xylitol, sorbitol, mannitol, maltose, inositol, trehalose, glucose; polymers such as: serum albumin (bovine serum albumin (BSA), human SA or recombinant HA), dextran, poly(viny alcohol) PVA, hydroxypropyl methylcellulose (HPMC), polyethyleneimine, gelatin, polyvinylpyrrolidone (PVP), hydroxyethylcellulose (HEC); non-aqueous solvents such as: polyhydric alcohols, (e.g., PEG, and glycerol) and dimethylformamide (DMF); amino acids such as: proline, L-serine, sodium glutamic acid, alanine, glycine, lysine hydrochloride, sarcosine and gamma-aminobutyric acid; surfactants such as: Tween®-80 (polysorbate 80), Tween®-20 (polysorbate 20), SDS, polysorbate, poloxamers; and miscellaneous excipients such as: potassium phosphate, sodium acetate, ammonium sulfate, magnesium sulfate, sodium sulfate, trimethylamine N-oxide, betaine, metal ions (e.g., zinc, calcium, and magnesium), CHAPS, monolaurate, 2-O-beta-mannoglycerate or any combination of the above.

Preferred excipients are sucrose, lactose, glycerol, xylitol, sorbitol, mannitol, maltose, inositol, trehalose, glucose, bovine serum albumin (BSA), human serum albumin (HSA), recombinant albumin, dextran, PVA, hydroxypropyl methylcellulose (HPMC), polyethyleneimine, gelatin, polyvinylpyrrolidone (PVP), hydroxyethylcellulose (HEC), polyethylene glycol, ethylene glycol, glycerol, alanine, glycine, lysine hydrochloride, sarcosine, SDS, polysorbate 20, polysorbate 80, poloxamer 188, trimethylamine N-oxide, betaine, zinc ions, calcium ions, magnesium ions, CHAPS, sucrose monolaurate, and 2-O-beta-mannoglycerate.

The concentration of one or more excipients in a formulation of the invention is/are preferably between about 0.001 to 5 weight percent, more preferably about 0.1 to 2 weight percent.

Methods of Treatment

In another embodiment, the invention provides a method of treating a mammal comprising administering a therapeutically effective amount of the pharmaceutical compositions of the invention to a mammal, wherein the mammal has a disease or disorder that can be beneficially treated with etanercept.

In a preferred embodiment, the etanercept is derived from the same species of mammal as is to be treated with the composition.

In a preferred embodiment, the mammal is a human.

Diseases or disorders that can be treated with the provided compositions include but are not limited to rheumatoid arthritis, psoriatic arthritis, ankylosing spondylitis, Wegener's disease (granulomatosis), Crohn's disease (or inflammatory bowel disease), chronic obstructive pulmonary disease (COPD), Hepatitis C, endometriosis, asthma, cachexia, psoriasis, and atopic dermatitis. Additional diseases or disorders that can be treated with the compositions of the present invention include those described in WO 00/62790, WO 01/62272, U.S. Patent Application No. 2001/0021380, and U.S. Pat. No. 7,648,702 B2, the relevant portions of which are incorporated herein by reference.

The provided pharmaceutical compositions may be administered to a subject in need of treatment by injection systemically, such as by intravenous injection; or by injection or application to the relevant site, such as by direct injection, or direct application to the site when the site is exposed in surgery; or by topical application.

In one embodiment, the invention provides a method of treatment and/or prevention of rheumatoid arthritis comprises administering to a mammal in need thereof a therapeutically effective amount of one of the provided etanercept compositions.

The therapeutically effective amount of the etanercept in the provided compositions will depend on the condition to be treated, the severity of the condition, prior therapy, and the patient's clinical history and response to the therapeutic agent. The proper dose can be adjusted according to the judgment of the attending physician such that it can be administered to the patient one time or over a series of administrations.

In one embodiment, the effective etanercept amount per adult dose is from about 1-500 mg/m$^2$, or from about 1-200 mg/m$^2$, or from about 1-40 mg/m$^2$ or about 5-25 mg/m$^2$.

Alternatively, a flat dose may be administered, whose amount may range from 2-500 mg/dose, 2-100 mg/dose or from about 10-80 mg/dose.

If the dose is to be administered more than one time per week, an exemplary dose range is the same as the foregoing described dose ranges or lower and preferably administered two or more times per week at a per dose range of 25-100 mg/dose.

In another embodiment, an acceptable dose for administration by injection contains 80-100 mg/dose, or alternatively, containing 80 mg per dose.

The dose can be administered weekly, biweekly, or separated by several weeks (for example 2 to 8).

In one embodiment, etanercept is administered at 25 to 75 mg/ml by a single subcutaneous (SC) injection.

In some instances, an improvement in a patient's condition will be obtained by administering a dose of up to about 100 mg of the pharmaceutical composition one to three times per week over a period of at least three weeks. Treatment for longer periods may be necessary to induce the desired degree of improvement. For incurable chronic conditions the regimen may be continued indefinitely. For pediatric patients (ages 4-17), a suitable regimen may involve administering a dose of 0.4 mg/kg to 5 mg/kg of etanercept, one or more times per week.

In another embodiment, the pharmaceutical formulations of the invention may be prepared in a bulk formulation, and as such, the components of the pharmaceutical composition are adjusted to be higher than would be required for administration and diluted appropriately prior to administration.

The pharmaceutical compositions can be administered as a sole therapeutic or in combination with additional therapies as needed. Thus, in one embodiment, the provided methods of treatment and/or prevention are used in combination with administering a therapeutically effective amount of another active agent. The other active agent may be administered before, during, or after administering the pharmaceutical compositions of the present invention. Another active agent may be administered either as a part of the provided compositions, or alternatively, as a separate formulation.

Administration of the provided pharmaceutical compositions can be achieved in various ways, including parenteral, oral, buccal, nasal, rectal, intraperitoneal, intradermal, transdermal, subcutaneous, intravenous, intra-arterial, intracardiac, intraventricular, intracranial, intratracheal, intrathecal administration, intramuscular injection, intravitreous injection, and topical application.

The pharmaceutical compositions of this invention are particularly useful for parenteral administration, i.e., subcutaneously, intramuscularly, intravenously, intraperitoneal, intracerebrospinal, intra-articular, intrasynovial, and/or intrathecal. Parenteral administration can be by bolus injection or continuous infusion. Pharmaceutical compositions for injection may be presented in unit dosage form, e.g., in ampoules or in multi-dose containers, with an added preservative. In addition, a number of recent drug delivery approaches have been developed and the pharmaceutical compositions of the present invention are suitable for administration using these new methods, e.g., Inject-ease®, Genject®, injector pens such as GenPen®, and needleless devices such as MediJector® and BioJector®. The present pharmaceutical composition can also be adapted for yet to be discovered administration methods. See also Langer, 1990, Science, 249:1527-1533.

The provided pharmaceutical compositions can also be formulated as a depot preparation. Such long acting formulations may be administered by implantation (for example subcutaneously or intramuscularly) or by intramuscular injection. Thus, for example, the formulations may be modified with suitable polymeric or hydrophobic materials (for example as an emulsion in an acceptable oil) or ion exchange resins, or as sparingly soluble derivatives, for example, as a sparingly soluble salt.

The pharmaceutical compositions may, if desired, be presented in a vial, pack or dispenser device which may contain one or more unit dosage forms containing the active ingredient. In one embodiment the dispenser device can comprise a syringe having a single dose of the liquid formulation ready for injection. The syringe can be accompanied by instructions for administration.

In another embodiment, the present invention is directed to a kit or container, which contains an aqueous pharmaceutical composition of the invention. The concentration of the polypeptide in the aqueous pharmaceutical composition can vary over a wide range, but is generally within the range of from about 0.05 to about 20,000 micrograms per milliliter (μg/ml) of aqueous formulation. The kit can also be accompanied by instructions for use.

The present invention is more particularly described in the following examples that are intended as illustrative only, since many modifications and variations therein will be apparent to those skilled in the art.

EXAMPLE 1A

Etanercept Stabilized with Serine

A stable aqueous pharmaceutical composition containing etanercept and serine (without arginine) was prepared as follows:

Each solid formulation component (buffer, amino acid, sugar, polyol etc) is weighed to the amount required for a given volume of formulation buffer. These components are combined into a beaker or vessel capable of carrying and measuring the given volume of formulation buffer. A volume of deionized water equal to approximately ¾ of the target given formulation buffer is added to the beaker, and the components solubilzed through use of a magnetic stir bar. The pH of the buffer is adjusted to the target formulation pH using 1 molar sodium hydroxide and/or 1 molar hydrogen chloride. The final formulation buffer volume is then raised to the target volume through the addition of deionized water. The solution is mixed with a magnetic stir bar after final water addition. Etanercept protein solution is placed in dialysis material housing (such as Thermo Scientific Slide-A-Lyzer MINI Dialysis Unit 10,000 MWCO), which is then placed in contact with the desired formulation buffer for 12 hours at 4° C. Formulation buffer volume to protein solution volume ratio should be no less than 1000:1. The dialysis housing and protein solution it contains is then placed in a second, equal volume of formulation buffer for an additional 12 hours at 4° C.

Resulting protein solution is removed from the dialysis material housing, and the concentration of protein determined using ultraviolet spectroscopy. Protein concentration is adjusted to the desired level using centrifugation (such as Amicon Ultra 10,000 MWCO Centrifugal Concentrators) and/or dilution with formulation buffer.

Five sample compositions of the invention in which etanercept is stabilized with serine (in the absence of arginine) are represented

| (Formulation 1:15) | |
|---|---|
| Ingredient | concentration |
| Etanercept (active ingredient) | 50 mg/ml |
| Serine (inactive ingredient) | 25 mM |
| Sodium phosphaye, pH 6.3 (inactive) | 25 mM |
| Sucrose (inactive) | 1% (w/v) |
| NaCl (inactive) | 100 mM |

| (Formulation 1:12) | |
|---|---|
| Ingredient | concentration |
| Etanercept (active ingredient) | 50 mg/ml |
| Serine (inactive ingredient) | 25 mM |
| Sodium phosphate, pH 6.4 (inactive) | 25 mM |
| Sucrose (inactive) | 2.5% (w/v) or 5% (w/v) |
| NaCl (inactive) | 100 mM |

| (Formulation 1:16) | |
|---|---|
| Ingredient | concentration |
| Etanercept (active ingredient) | 50 mg/ml |
| Serine (inactive ingredient) | 50 mM |
| Sodium phosphaye, pH 6.4 (inactive) | 25 mM |
| Sucrose (inactive) | 5% (w/v) |
| NaCl (inactive) | 25 mM |

| (Formulation 2:4) | |
|---|---|
| Ingredient | concentration |
| Etanercept (active ingredient) | 50 mg/ml |
| Serine (inactive ingredient) | 100 mM |
| Sodium phosphaye, pH 6.3 (inactive) | 25 mM |
| Sucrose (inactive) | 1% (w/v) |

| (Formulation 3:8) | |
|---|---|
| Ingredient | concentration |
| Etanercept (active ingredient) | 50 mg/ml |
| Serine (inactive ingredient) | 120 mM |
| Sodium phosphaye, pH 6.3 (inactive) | 25 mM |
| Sucrose (inactive) | 1% (w/v) |

The compositions can be tested for long-term stability by size exclusion chromatography (SEC), denatured SEC (dSEC), hydrophobic interaction chromatography (HIC), sodium dodecylsulfate polyacrylamide gel electrophoresis (SDS-PAGE), and for binding and bioactivity at various timepoints. The bioactivity can be measured by any number of well-known assays including by SEC, dSEC, HIC, as discussed below.

For example, the techniques of Size Exclusion Chromatography are described in Hawe et al, Pharm. Res. 2011, 28: 2302 and/or van Marrschalkerweerd et al., Eur. J. Pharm. Biopharm. 2011, 78: 213. Similarly, the techniques of Denatured Size Exclusion Chromatography, Hydrophobic Interaction Chromatography, and Sodium DodecylSulfate-Poly-Acrylamide Gel Electrophoresis are also well known to persons having ordinary skill in the art.

It is believed that the composition will be stable over the term of two years or more.

EXAMPLE 1B

Etanercept Stabilized with Proline

Compositions stabilized with Proline in this Example 1B may be prepared and tested using the procedures similar to those described in Example 1A. Etanercept formulations using proline for stabilization, exemplified below, do not contain arginine.

| (Formulation 1:4) | |
|---|---|
| Ingredient | concentration |
| Etanercept (active ingredient) | 50 mg/ml |
| Proline (inactive ingredient) | 25 mM |
| Sodium phosphate, pH 6.3 (inactive) | 25 mM |
| Sucrose (inactive) | 2.5% (w/v) |
| NaCl (inactive) | 50 mM |

| (Formulation 1:5) | |
|---|---|
| Ingredient | concentration |
| Etanercept (active ingredient) | 50 mg/ml |
| Proline (inactive ingredient) | 50 mM |
| Sodium phosphate, pH 6.3 (inactive) | 25 mM |
| Sucrose (inactive) | 1.0% (w/v) |
| NaCl (inactive) | 25 mM |

| (Formulation 1:6) | |
|---|---|
| Ingredient | concentration |
| Etanercept (active ingredient) | 50 mg/ml |
| Proline (inactive ingredient) | 100 mM |
| Sodium phosphate, pH 6.3 (inactive) | 25 mM |
| Sucrose (inactive) | 1.0% (w/v) |

The compositions can be tested for long-term stability, and the bioactivity can be measured in the same fashion as discussed in Example 1A.

It is believed that the compositions will be stable over the term of two years or more.

EXAMPLE 1C

Etanercept Stabilized with Glutamate

Compositions stabilized with glutamate may be prepared and tested using the procedures similar to those described in Example 1A.

Glutamate stabilized etanercept compositions, containing no arginine, are exemplified below:

| (Formulation 1:9) | |
|---|---|
| Ingredient | concentration |
| Etanercept (active ingredient) | 50 mg/ml |
| Glutamate (inactive ingredient) | 25 mM |
| Sodium phosphate, pH 6.3 (inactive) | 25 mM |
| Sucrose (inactive) | 1% (w/v) |
| NaCl (inactive) | 100 mM |

| (Formulation 2:2) | |
|---|---|
| Ingredient | concentration |
| Etanercept (active ingredient) | 50 mg/ml |
| Glutamate (inactive ingredient) | 50 mM |
| Sodium phosphate, pH 6.3 (inactive) | 25 mM |
| Sucrose (inactive) | 1% (w/v) |
| NaCl (inactive) | 50 mM |

| (Formulation 2:3) | |
|---|---|
| Ingredient | concentration |
| Etanercept (active ingredient) | 50 mg/ml |
| Glutamate (inactive ingredient) | 100 mM |
| Sodium phosphate, pH 6.3 (inactive) | 25 mM |
| Sucrose (inactive) | 1% (w/v) |

| (Formulation 3:5) | |
|---|---|
| Ingredient | concentration |
| Etanercept (active ingredient) | 50 mg/ml |
| Glutamate (inactive ingredient) | 120 mM |
| Sodium phosphate, pH 6.5 (inactive) | 25 mM |
| Sucrose (inactive) | 1% (w/v) |

The composition can be tested for long-term stability, and the bioactivity can be measured in the same fashion as discussed in Example 1A.

It is believed that the composition will be stable over the term of two years or more.

EXAMPLE 2A

Etanercept Stabilized with Calcium Chloride

Etanercept formulations stabilized with calcium chloride may be prepared and tested using the procedures similar to those described in Example 1A.

Etanercept compositions stabilized with calcium chloride, and containing no arginine, are exemplified below.

| (Formulation P1:1) | |
|---|---|
| Ingredient | concentration |
| Etanercept (active ingredient) | 50 mg/ml |
| Calcium chloride (inactive ingredient) | 2 mM |
| Sodium phosphate, pH 6.3 (inactive) | 25 mM |

| (Formulation 1:11) | |
|---|---|
| Ingredient | concentration |
| Etanercept (active ingredient) | 50 mg/ml |
| Calcium chloride (inactive ingredient) | 2 mM |
| Sodium phosphate, pH 6.3 (inactive) | 25 mM |
| NaCl (inactive) | 100 mM |
| Sucrose (inert) | 2.5% (w/v) |

| (Formulation 1:18) | |
|---|---|
| Ingredient | concentration |
| Etanercept (active ingredient) | 50 mg/ml |
| Calcium chloride (inactive ingredient) | 2 mM |
| Sodium phosphate, pH 6.3 (inactive) | 25 mM |
| Xylitol (inactive) | 10 mM |

| (Formulation 3:6) | |
|---|---|
| Ingredient | concentration |
| Etanercept (active ingredient) | 50 mg/ml |
| Calcium chloride (inactive ingredient) | 2 mM |
| Sodium phosphate, pH 6.3 (inactive) | 15 mM |
| NaCl (inactive) | 75 mM |
| Sucrose (inactive) | 3% (w/v) |

| (Formulation 3:9) | |
|---|---|
| Ingredient | concentration |
| Etanercept (active ingredient) | 50 mg/ml |
| Calcium chloride (inactive ingredient) | 1 mM |
| Sodium phosphate, pH 6.6 (inactive) | 10 mM |
| NaCl (inactive) | 50 mM |
| Trehalose (inactive) | 5% (w/v) |

| (Formulation P1:2) | |
|---|---|
| Ingredient | concentration |
| Etanercept (active ingredient) | 50 mg/ml |
| Magnesium chloride (inactive ingredient) | 2 mM |
| Sodium phosphate, pH 6.3 (inactive) | 25 mM |

| (Formulation 2:15) | |
|---|---|
| Ingredient | concentration |
| Etanercept (active ingredient) | 50 mg/ml |
| Magnesium chloride (inactive ingredient) | 4 mM |
| Sodium phosphate, pH 6.4 (inactive) | 25 mM |
| NaCl (inactive) | 100 mM |
| Sucrose (inactive) | 2.5% (w/v) |

| (Formulation 3:7) | |
|---|---|
| Ingredient | concentration |
| Etanercept (active ingredient) | 50 mg/ml |
| Magnesium chloride (inactive ingredient) | 5 mM |
| Sodium phosphate, pH 6.3 (inactive) | 15 mM |
| NaCl (inactive) | 75 mM |
| Sucrose (inactive) | 2.5% (w/v) |

| (Formulation 3:14) | |
|---|---|
| Ingredient | concentration |
| Etanercept (active ingredient) | 50 mg/ml |
| Magnesium chloride (inactive ingredient) | 10 mM |
| Sodium phosphate, pH 6.3 (inactive) | 25 mM |
| NaCl (inactive) | 110 mM |
| Sucrose (inactive) | 1% (w/v) |

| (Formulation 4:2) | |
|---|---|
| Ingredient | concentration |
| Etanercept (active ingredient) | 50 mg/ml |
| Magnesium chloride (inactive ingredient) | 10 mM |
| Sodium phosphate, pH 6.5 (inactive) | 15 mM |
| NaCl (inactive) | 75 mM |
| Sucrose (inactive) | 3% (w/v) |

The composition can be tested for long-term stability, and the bioactivity can be measured in the same fashion as discussed in Example 1A.

It is believed that the composition will be stable over the term of two years or more.

EXAMPLE 2B

Etanercept Stabilized with Magnesium Chloride

Etanercept formulations stabilized with magnesium chloride may be prepared and tested using the procedures similar to those described in Example 1A. The etanercept formulations exemplified below do not contain arginine.

The composition can be tested for long-term stability, and the bioactivity can be measured in the same fashion as discussed in Example 1A.

It is believed that the composition will be stable over the term of two years or more.

EXAMPLE 2C

Etanercept Stabilized with Zinc Chloride

Etanercept formulations stabilized with zinc chloride may be prepared and tested using the procedures similar to those described in Example 1A.

The etanercept formulation exemplified below does not contain arginine.

(Formulation P1:3)

| Ingredient | concentration |
|---|---|
| Etanercept (active ingredient) | 50 mg/ml |
| Zinc chloride (inactive ingredient) | 2 mM |
| Sodium phosphate, pH 6.3 (inactive) | 25 mM |

The composition can be tested for long-term stability, and the bioactivity can be measured in the same fashion as discussed in Example 1A.

It is believed that the composition will be stable over the term of two years or more.

EXAMPLE 3A

Etanercept Stabilized with Meglumine

Etanercept compositions stabilized with Meglumine may be prepared and tested using the procedures similar to those described in Example 1A. Meglumine stabilized etanercept compositions, exemplified below, do not contain arginine.

(Formulation 1:19)

| Ingredient | concentration |
|---|---|
| Etanercept (active ingredient) | 50 mg/ml |
| Meglumine (inactive ingredient) | 5% (w/v) |
| Sodium phosphate, pH 6.3 (inactive) | 25 mM |

(Formulation 1:21)

| Ingredient | concentration |
|---|---|
| Etanercept (active ingredient) | 50 mg/ml |
| Meglumine (inactive ingredient) | 0.49% (w/v) |
| Sodium phosphate, pH 6.3 (inactive) | 25 mM |
| Sucrose (inactive) | 1% (w/v) |
| NaCl (inactive) | 100 mM |

The composition can be tested for long-term stability, and the bioactivity can be measured in the same fashion as discussed in Example 1A.

It is believed that the composition will be stable over the term of two years or more.

EXAMPLE 3B

Etanercept Stabilized with a Derivative of Mannitol

Etanercept compositions stabilized with a derivative of mannitol may be prepared and tested using the procedures similar to those described in Example 1A.

The formulation exemplified below does not contain arginine:

| Ingredient | % by weight |
|---|---|
| Etanercept (active ingredient) | 50 mg/ml |
| Mannosylglycerate (inactive ingredient) | 4% (w/v) |

The composition can be tested for long-term stability, and the bioactivity can be measured in the same fashion as discussed in Example 1A.

It is believed that the composition will be stable over the term of two years or more.

EXAMPLE 4A

Etanercept Stabilized with Trehalose (or Sucrose) and Mannitol

Etanercept compositions stabilized with mannitol in combination with trehalose (or sucrose), may be prepared and tested using the procedures similar to those described in Example 1A. The stabilized formulations exemplified below do not contain arginine.

(Formulation P1:5)

| Ingredient | concentration |
|---|---|
| Etanercept (active ingredient) | 50 mg/ml |
| Trehalose (inactive ingredient) | 4% (w/v/) |
| Mannitol (inactive) | 2% (w/v/) |

(Formulation 1:10)

| Ingredient | concentration |
|---|---|
| Etanercept (active ingredient) | 50 mg/ml |
| Sodium phosphate, pH 6.32 (inactive) | 25 mM |
| Sucrose (inactive) | 5% (w/v) |
| Mannitol (inactive) | 2% (w/v) |

The composition can be tested for long-term stability, and the bioactivity can be measured in the same fashion as discussed in Example 1A.

It is believed that the composition will be stable over the term of two years or more.

EXAMPLE 4B

Etanercept Stabilized with Sucrose and Sorbitol

Etanercept compositions stabilized with a combination of sucrose and sorbitol may be prepared and tested using the procedures similar to those described in Example 1A. The formulation exemplified below does not contain arginine.

| Ingredient | concentration |
|---|---|
| Etanercept (active ingredient) | 50 mg/ml |
| Sucrose (inactive ingredient) | 4% (w/v) |
| Sorbitol (inactive) | 2% (w/v) |
| Sodium phosphate, pH 6.3 (inactive) | 25 mM |

The composition can be tested for long-term stability, and the bioactivity can be measured in the same fashion as discussed in Example 1A.

It is believed that the composition will be stable over the term of two years or more.

EXAMPLE 5

Etanercept Stabilized with Xylitol

Etanercept formulations stabilized with xylitol may be prepared and tested using the procedures similar to those described in Example 1A. The compositions exemplified below do not contain arginine.

(Formulation 1:17)

| Ingredient | concentration |
| --- | --- |
| Etanercept (active ingredient) | 50 mg/ml |
| Sodium phosphate, pH 6.3 (inactive) | 25 mM |
| Xylitol (inactive) | 10% (w/v) |

(Formulation 2:10)

| Ingredient | concentration |
| --- | --- |
| Etanercept (active ingredient) | 50 mg/ml |
| Sodium phosphate, pH 6.31 (inactive) | 25 mM |
| Xylitol (inactive) | 6% (w/v) |

(Formulation 2:11)

| Ingredient | concentration |
| --- | --- |
| Etanercept (active ingredient) | 50 mg/ml |
| Sodium phosphate, pH 6.3 (inactive) | 25 mM |
| Xylitol (inactive) | 2.5% (w/v) |
| Sucrose (inactive ingredient) | 5% (w/v) |

(Formulation 2:18)

| Ingredient | concentration |
| --- | --- |
| Etanercept (active ingredient) | 50 mg/ml |
| Sodium phosphate, pH 6.4 (inactive) | 25 mM |
| Xylitol (inactive) | 2.5% (w/v) |
| Meglumine (inactive) | 2.5% (w/v) |

(Formulation 2:19)

| Ingredient | concentration |
| --- | --- |
| Etanercept (active ingredient) | 50 mg/ml |
| Sodium phosphate, pH 6.24 (inactive) | 10 mM |
| Xylitol (inactive) | 2.5% (w/v) |
| Meglumine (inactive) | 2.5% (w/v) |
| NaCl (inactive) | 2.5% (w/v) |
| Sucrose (inactive) | 1% (w/v) |

EXAMPLE 6

Etanercept Stabilized with NaCl

Etanercept formulations stabilized with NaCl, alone, or NaCl in combination with sucrose, trehalose and/or arginine, may be prepared and tested using the procedures similar to those described in Example 1A. With the exception of formulation 3:13 below, the compositions exemplified below do not contain arginine.

(Formulation 2:8)

| Ingredient | concentration |
| --- | --- |
| Etanercept (active ingredient) | 50 mg/ml |
| Sodium phosphate, pH 6.32 (inactive) | 25 mM |
| NaCl (inactive) | 150 mM |

(Formulation 2:6)

| Ingredient | concentration |
| --- | --- |
| Etanercept (active ingredient) | 50 mg/ml |
| Sodium phosphate, pH 6.3 (inactive) | 15 mM |
| NaCl (inactive) | 100 mM |
| Sucrose (inactive) | 2% (w/v) |

(Formulation 3:10)

| Ingredient | concentration |
| --- | --- |
| Etanercept (active ingredient) | 50 mg/ml |
| Sodium phosphate, pH 6.57 (inactive) | 10 mM |
| NaCl (inactive) | 75 mM |
| Sucrose (inactive) | 3% (w/v) |

(Formulation 3:11)

| Ingredient | concentration |
| --- | --- |
| Etanercept (active ingredient) | 50 mg/ml |
| Sodium phosphate, pH 6.30 (inactive) | 25 mM |
| NaCl (inactive) | 75 mM |
| Trehalose (inactive) | 3% (w/v) |

(Formulation 3:12)

| Ingredient | concentration |
| --- | --- |
| Etanercept (active ingredient) | 50 mg/ml |
| Sodium phosphate, pH 6.3 (inactive) | 25 mM |
| NaCl (inactive) | 75 mM |
| Sucrose (inactive) | 3% (w/v) |

(Formulation 3:13)

| Ingredient | concentration |
| --- | --- |
| Etanercept (active ingredient) | 50 mg/ml |
| Sodium phosphate, pH 6.3 (inactive) | 25 mM |
| NaCl (inactive) | 120 mM |
| Sucrose (inactive) | 1% (w/v) |
| Arginine (inactive) | 5 mM |

The compositions can be tested for long-term stability, and the bioactivity can be measured in the same fashion as discussed in Example 1A.

The foregoing description of the exemplary embodiments of the invention has been presented only for the purposes of illustration and description and is not intended to be exhaustive or to limit the invention to the precise forms disclosed. Many modifications and variations are possible in light of the above teaching.

Analysis of Etanercept Formulations

A. Thermal Stability Storage

Following dialysis and concentration, samples of the etanercept formulations exemplified above were sterile filtered in a bio safety cabinet. Using sterilized pipettes and autoclaved pipette tips, samples of the etanercept formulations were transferred to pre-labeled and autoclaved 1 mL lyophilization vials. Vials were stoppered with sterile butyl stoppers and crimped with aluminum caps. All vials were then transferred to thermal stability ovens. Samples were subject to two thermal stability regimes: (1) two weeks at 40° C. and (2) four weeks at 25° C. Throughout this specification, these two temperature regimes are denoted "$T_2$" and "$T_4$," respectively.

B. Size Exclusion Chromatography (SEC)

Etanercept formulations disclosed herein were analyzed using the well known technique of Size Exclusion Chromatography (SEC), a high-performance liquid chromatography method in which analytes are separated by size (see Rogner, M. (2000). Size Exclusion Chromatography. *Protein Liquid Chromatography*. M. Kastner. Amsterdam, Elsevier. 61: 89-145.). In order to evaluate thermal stability of the Etanercept samples described above, the samples were examined by a SEC method based on the literature (van Maarschalkerweerd, A., G. J. Wolbink, et al. (2011). "Comparison of analytical methods to detect instability of etanercept during thermal stress testing." *European Journal of Pharmaceutics and Biopharmaceutics* 78(2): 213-221.) The mobile phase buffer was prepared to contain 50 mM sodium phosphate monobasic monohydrate and 150 mM arginine. The pH was adjusted to 6.5 using 1 M HCl. All separations were performed using a Tosoh TSK-Gel SWxl 6 mm×4 cm guard column (cat. no. 8543) attached linearly to a Tosoh TSK-Gel G4000 SWxl 7.8 mm×30 cm (cat. no. 8542). To perform a separation, the columns were brought to room temperature (23° C.) and equilibrated with mobile phase at a flow rate of 0.5 mL/min. 5 microliters of 50 mg/mL etanercept formulation were injected onto the column using an autosampler. The separation was accomplished over 30 minutes at a flow rate of 0.5 mL/minute. Column eluent was monitored at a wavelength of 280 nm during this time.

C. Integration of Size Exclusion Chromatography Chromatograms

All integration was performed using Chromeleon software (Dionex). Prior to integration, the SEC chromatogram for a buffer containing no etanercept was subtracted from all chromatograms. All integration was performed between retention times of 12 minutes and 26 minutes. Several parameters were used to define a peak. The minimum area for a detected peak was set to 0.05 mAu*min. The two-dimensional sensitivity for peak detection was set to 0.01 mAu and 75 seconds. Peak shoulders were added manually using a manual integration tool. All detected peaks were manually adjusted in two steps. First, peak baselines (the bottom boundary of the peak) were adjusted to horizontal. Secondly, the vertical positions of the peak baselines were adjusted to that of the chromatogram baseline. The chromatogram baseline value was defined as the signal in absence of analyte. The signal in absence of analyte was defined as the absorbance in mAu at 12 minutes retention time.

D. SEC Fractions of Etanercept Formulations

In the SEC analysis of etanercept formulations described above, three SEC chromatography fractions were identified and studied. The fractions that were analyzed were, in the order of elution from the SEC column: (1) a very high molecular weight fraction representing aggregates of the intact etanercept TNFR:FC fusion protein likely assembled via non-covalent electrostatic attraction among intact etanercept molecules (hereinafter "aggregate(s)" or aggregate(s) content); (2) monomer content, representing the intact etanercept TNFR:FC fusion protein (hereinafter referred to as "monomer" of "monomer content"); (3) a fraction likely representing one fragment or a population of fragments of the etanercept molecule in which one portion of the TNFR: molecule fusion protein has become disassociated from the monomer; such as for example dissociation of an arm of the FC portion of the fusion protein at the hinge region of the molecule (hereinafter referred to as "Fragment 3"). The following table shows the relative amounts of Aggregates, Monomer and Fragment 3 determined by SEC analysis as described above.

TABLE 1

SEC ANALYSIS OF MONOMER

| Formulation No. | $t_0$ | $t_1$ | $t_2$ |
|---|---|---|---|
| Commercial Enbrel ® (comparative) [1:2] | 98.81 | 92.58 | 87.64 |
| 1:5 | 98.38 | 91.65 | 86.89 |
| 1:9 | 98.48 | 92.05 | 86.06 |
| 1:10 | 98.25 | 91.84 | 84.51 |
| 1:11 | 98.60 | 92.08 | 89.71 |
| 1:17 | 98.02 | 93.90 | 87.53 |
| 1:18 | 98.27 | 92.89 | 88.21 |
| 1:19 | 98.10 | 91.94 | 86.06 |
| 1:21 | 98.22 | 90.78 | 85.43 |
| 2:2 | 98.11 | — | 86.92 |
| 2:3 | 98.14 | — | 88.84 |
| 2:4 | 98.12 | — | 88.16 |
| 2:6 | 98.09 | — | 87.77 |
| 2:8 | 98.07 | — | 88.38 |
| 2:10 | 98.09 | — | 87.56 |
| 2:11 | 98.10 | — | 88.03 |
| 2:15 | 98.18 | — | 88.22 |
| 2:18 | 98.10 | — | 89.19 |
| 2:19 | 98.19 | — | 89.63 |
| 3:5 | 98.35 | — | 90.75 |
| 3:6 | 98.07 | — | 90.75 |
| 3:7 | 98.09 | — | 89.60 |
| 3:8 | 98.15 | — | 89.27 |
| 3:9 | 97.90 | — | 91.44 |
| 3:10 | 98.16 | — | 89.77 |
| 3:11 | 98.32 | — | 89.87 |
| 3:12 | 98.33 | — | 90.92 |
| 3:13 | 98.18 | — | 90.74 |
| 3:14 | 98.22 | — | 90.54 |
| 4:2 | 98.62 | — | 90.47 |

Note:
Amounts reported Tables I, II and III are percentages by weight
$T_0$ = formulation maintained at 5 C. and analyzed within 24 hours of creation.
$T_1$ = formulation stored for one week at 40° C.
$T_2$ = formulation stored for two weeks at 40 C.

TABLE II

SEC ANALYSIS OF AGGREGATES

| Formulation No. | $t_0$ | $t_1$ | $t_2$ |
|---|---|---|---|
| Commercial Enbrel ® (comparative) | 0.09 | 0.59 | 1.02 |
| 1:5 | 0.23 | 0.63 | 1.01 |
| 1:9 | 0.18 | 0.67 | 2.20 |
| 1:10 | 0.26 | 0.68 | 0.82 |
| 1:11 | 0.12 | 0.50 | 0.64 |

TABLE II-continued

SEC ANALYSIS OF AGGREGATES

| Formulation No. | $t_0$ | $t_1$ | $t_2$ |
|---|---|---|---|
| 1:17 | 0.31 | 0.70 | 2.17 |
| 1:18 | 0.24 | 0.65 | 1.61 |
| 1:19 | 0.26 | 0.63 | 1.50 |
| 1:21 | 0.23 | 0.64 | 1.30 |
| 2:2 | 0.29 | — | 3.53 |
| 2:3 | 0.29 | — | 2.31 |
| 2:4 | 0.29 | — | 2.29 |
| 2:6 | 0.30 | — | 1.81 |
| 2:8 | 0.30 | — | 1.42 |
| 2:10 | 0.29 | — | 2.57 |
| 2:11 | 0.31 | — | 1.68 |
| 2:15 | 0.27 | — | 1.83 |
| 2:18 | 0.29 | — | 1.53 |
| 2:19 | 0.26 | — | 1.24 |
| 3:5 | 0.28 | — | 0.99 |
| 3:6 | 0.23 | — | 1.27 |
| 3:7 | 0.28 | — | 0.93 |
| 3:8 | 0.28 | — | 1.60 |
| 3:9 | 0.37 | — | 0.73 |
| 3:10 | 0.27 | — | 1.33 |
| 3:11 | 0.20 | — | 1.24 |
| 3:12 | 0.21 | — | 0.85 |
| 3:13 | 0.28 | — | 0.86 |
| 3:14 | 0.25 | — | 0.91 |
| 4:2 |  |  | 1.56 |

TABLE III

ANALYSIS OF FRAGMENT 3

| Formulation No | $t_0$ | $t_1$ | $t_2$ |
|---|---|---|---|
| Commercial Enbrel ® (comparative) | 0.00 | 3.30 | 6.29 |
| 1:5 | 0.00 | 4.43 | 6.64 |
| 1:9 | 0.00 | 3.96 | 6.34 |
| 1:10 | 0.00 | 3.78 | 8.04 |
| 1:11 | 0.00 | 3.92 | 4.71 |
| 1:17 | 0.00 | 2.33 | 4.10 |
| 1:18 | 0.00 | 3.05 | 4.65 |
| 1:19 | 0.00 | 3.82 | 6.73 |
| 1:21 | 0.00 | 4.92 | 7.37 |
| 2:2 | 0.00 | — | 4.67 |
| 2:3 | 0.00 | — | 3.61 |
| 2:4 | 0.00 | — | 3.61 |
| 2:6 | 0.00 | — | 4.73 |
| 2:8 | 0.00 | — | 6.29 |
| 2:10 | 0.00 | — | 5.10 |
| 2:11 | 0.00 | — | 5.68 |
| 2:15 | 0.00 | — | 5.56 |
| 2:18 | 0.00 | — | 4.24 |
| 2:19 | 0.00 | — | 4.34 |
| 3:5 | 0 | — | 3.15 |
| 3:6 | 0 | — | 4.72 |
| 3:7 | 0 | — | 4.37 |
| 3:8 | 0 | — | 3.61 |
| 3:9 | 0 | — | 3.48 |
| 3:10 | 0 | — | 3.76 |
| 3:11 | 0 | — | 3.59 |
| 3:12 | 0 | — | 3.68 |
| 3:13 | 0 | — | 3.88 |
| 3:14 | 0 | — | 3.83 |
| 4:2 |  |  | 5.40 |

TABLE IV

SEC MONOMER CONTENT (4 weeks/25° C.)

| FORMULATION No. | $T_0$ Monomer Content | $T_4$ Monomer Content |
|---|---|---|
| Commercial Enbrel ® (comparative) | 98.15 | 97.86 |
| 3:5 | 98.35 | 95.16 |
| 3:6 | 98.07 | 94.84 |
| 3:7 | 98.09 | 97.75 |
| 3:8 | 98.15 | 97.65 |
| 3:9 | 97.90 | 97.44 |
| 3:10 | 98.16 | 97.66 |
| 3:11 | 98.32 | 97.75 |
| 3:12 | 98.33 | 97.90 |
| 3:13 | 98.18 | 97.78 |
| 3:14 | 98.22 | 97.79 |
| 4:2 | 98.62 | 94.70 |

Table IV below shows monomer (etanercept) content of etanercept formulations prepared according to the present invention, when stored for four weeks at 25 C.°-denoted by the symbol $T_4$. In the following table $T_0$ represents SEC measurements conducted within 24 hours of formulation preparation, at sample temperature of 5° C.; and $T_4$ represents etanercept formulation samples subjected to SEC analysis after 4 weeks storage at 25° C.

TABLE V

SEC AGGREGATES CONTENT (4 weeks/25° C.)

| FORMULATION No. | $T_0$ Aggregate(s) Content | $T_4$ Aggregate(s) Content |
|---|---|---|
| Commercial Enbrel ® (comparative) | 0.28 | 0.25 |
| 3:5 | — | 0.50 |
| 3:6 | — | 0.57 |
| 3:7 | 0.28 | 0.31 |
| 3:8 | 0.28 | 0.37 |
| 3:9 | 0.37 | 0.41 |
| 3:10 | 0.27 | 0.32 |
| 3:11 | 0.20 | 0.27 |
| 3:12 | 0.21 | 0.26 |
| 3:13 | 0.28 | 0.32 |
| 3:14 | 0.25 | 0.28 |
| 4:2 | — | 0.57 |

Table V below shows aggregate(s) content of etanercept formulations prepared according to the present invention after storage for four weeks at 25 C.°. In the following table $T_0$ represents SEC measurements conducted within 24 hours of formulation preparation, at sample temperature of 5° C.; and $T_4$ represents etanercept formulation samples subjected to SEC analysis after 4 weeks storage at 25° C.

HIC Analysis of Etanercept Formulations

The following tables (Tables VI and VII) show the results of hydrophobic interaction chromatography ("HIC chromatography") conducted on samples 3:5 through 3:14. HIC chromatography was carried out in the manner described in U.S. Pat. No. 7,294,481, incorporated herein by reference. Samples were evaluated at $t_0$ (within 24 hours of preparation at 5° C.) and again after either two weeks of storage at 25° C. ($t_2$) (see Table VI) or after 4 weeks of storage at 25° C. ($t_4$)(See Table VII) Peak 1 is believed to be or include "Fragment 3" referenced above in the discussion of SEC data; Peak 2 is etanercept monomer as referenced above in the discussion of SEC data; and Peak 3 represents or includes "Aggregate(s)" as referenced above in the discussion of SEC data. It should further be understood that the terms "peak 1", "peak 2" and "peak 3" as used here also constitute a reference to the HIC peak 1, peak 2 and peaks referred to and disclosed in FIG. 4 of U.S. Pat. No. 7,294,481 incorporated herein by reference.

TABLE VI

HIC Data after Two Weeks Storage at 40° C.

| Form. # | PEAK 1 | | PEAK 2 | | PEAK 3 | |
|---|---|---|---|---|---|---|
| | $T_0$ | $T_2$ | $T_0$ | $T_2$ | $T_0$ | $T_2$ |
| Commercial Enbrel ® (comparative) | 0.91 | 3.23 | 86.72 | 83.41 | 12.33 | 13.36 |
| 3:5 | 0.72 | 2.95 | 85.82 | 82.50 | 13.45 | 14.55 |
| 3:6 | 0.72 | 3.44 | 85.91 | 83.26 | 13.36 | 13.30 |
| 3:7 | 0.74 | 3.52 | 86.11 | 82.41 | 13.15 | 14.07 |
| 3:8 | 0.72 | 3.08 | 85.80 | 83.90 | 13.48 | 13.02 |
| 3:9 | 0.69 | 2.39 | 90.93 | 85.09 | 8.38 | 12.52 |
| 3:10 | 0.74 | 3.06 | 87.36 | 84.24 | 11.90 | 12.70 |
| 3:11 | 0.56 | 3.10 | 86.46 | 83.73 | 12.98 | 13.18 |
| 3:12 | 0.68 | 3.07 | 86.80 | 83.52 | 12.52 | 13.40 |
| 3:13 | 0.77 | 2.86 | 86.45 | 84.33 | 12.78 | 12.82 |
| 3:14 | 0.71 | 2.51 | 87.14 | 84.54 | 12.15 | 12.95 |

TABLE VII

HIC Data after Storage at 25° C. for 4 Weeks

| Form. # | PEAK 1 | | PEAK 2 | | PEAK 3 | |
|---|---|---|---|---|---|---|
| | $T_0$ | $T_4$ | $T_0$ | $T_4$ | $T_0$ | $T_4$ |
| Commercial Enbrel ® (comparative) | 0.91 | 1.09 | 86.76 | 86.95 | 12.33 | 11.97 |
| 3:5 | 0.54 | 1.10 | 85.12 | 84.06 | 14.33 | 14.84 |
| 3:6 | 0.55 | 1.40 | 85.50 | 84.07 | 13.96 | 14.53 |
| 3:7 | 0.74 | 1.63 | 86.11 | 85.65 | 13.15 | 12.72 |
| 3:8 | 0.72 | 1.20 | 85.80 | 85.98 | 13.48 | 12.82 |
| 3:9 | 0.69 | 1.05 | 90.938 | 6.46 | 8.38 | 12.50 |
| 3:10 | 0.74 | 1.03 | 87.36 | 85.83 | 11.90 | 13.14 |
| 3:11 | 0.56 | 1.11 | 86.46 | 85.32 | 12.98 | 13.57 |
| 3:12 | 0.68 | 0.81 | 86.80 | 86.36 | 12.52 | 12.83 |
| 3:13 | 0.77 | 1.01 | 86.45 | 85.78 | 12.78 | 13.21 |
| 3:14 | 0.71 | 1.13 | 87.14 | 85.58 | 12.15 | 13.29 |
| 4:2 | 0.63 | 1.38 | 85.16 | 84.38 | 14.21 | 14.25 |

Other embodiments of the invention will be apparent to those skilled in the art from consideration of the specification and practice of the invention disclosed herein. It is intended that the specification and examples be considered as exemplary only, with a true scope and spirit of the invention being indicated by the following claims.

The ASCII text file "Sequence.txt" created on March 10, 2015, having the size of 4.5 KB, is incorporated by reference into the specification.

What is claimed is:

1. A stabilized aqueous pharmaceutical composition having long term storage stability, comprising: etanercept and a stabilizer to inhibit instability, aggregation and/or fragmentation of the etanercept, wherein the composition is free of arginine as a stabilizer and wherein the stabilizer is 1 mM to 20 mM magnesium chloride.

2. The stabilized composition of claim 1 characterized by:
(a) an SEC (size exclusion chromatography) analysis at $T_4$ of greater than 90, 91, 92, 93, 94, 95, 96, or 97 wt. % monomer content; and less than 3, 2 or 1 wt. % aggregate(s) content; and
(b) an HIC (hydrophobic interaction chromatography) analysis at $T_2$ wherein the amount of the composition represented by peak 1 of the HIC chromatogram is less than 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than 20, 19, 18, 17, 16, 15, 14, or 13 wt. %; and
(c) an HIC analysis at $T_4$ wherein the amount of the composition represented by peak 1 of the HIC chromatogram is less than 3, 2 or 1 wt. %; the amount of the composition represented by peak 2 of the HIC chromatogram is greater than 80, 81, 82, 83, 84 or 85 wt. %; and the amount of the composition represented by peak 3 of the HIC chromatogram is less than 20, 19, 18, 17, 16, 15, 14 or 13 wt. %.

3. The stabilized composition of claim 2 having an HIC analysis at $T_4$ or $T_2$ wherein the amount of the composition represented by peak 1 of the HIC chromatogram is less than 2 wt. %; the amount of the composition represented by peak 2 of the HIC chromatogram is greater than 85 wt. %; and the amount of the composition represented by peak 3 of the HIC chromatogram is less than 13 wt. %.

4. The stabilized composition of claim 1 wherein the composition comprises 25 to 50 mg/ml of etanercept; optionally up to 6 wt. % sucrose; 25 to 150 mM NaCl; and 1 to 30 mM sodium phosphate and wherein the composition has a pH of 6.0 to pH 7.0.

* * * * *